(12) United States Patent
Wittek et al.

(10) Patent No.: US 10,858,587 B2
(45) Date of Patent: *Dec. 8, 2020

(54) LIQUID-CRYSTALLINE MEDIUM, COMPOUNDS, AND HIGH-FREQUENCY COMPONENTS

(71) Applicant: MERCK PATENT GMBH, Darmstadt (DE)

(72) Inventors: Michael Wittek, Erzhausen (DE); Dagmar Klass, Darmstadt (DE)

(73) Assignee: MERCK PATENT GMBH, Darmstadt (DE)

(*) Notice: Subject to any disclaimer, the term of this patent is extended or adjusted under 35 U.S.C. 154(b) by 45 days.

This patent is subject to a terminal disclaimer.

(21) Appl. No.: 15/787,158

(22) Filed: Oct. 18, 2017

(65) Prior Publication Data

US 2018/0105748 A1 Apr. 19, 2018

(30) Foreign Application Priority Data

Oct. 18, 2016 (EP) ..................... 16194405

(51) Int. Cl.
C09K 19/30 (2006.01)
C09K 19/12 (2006.01)
C07C 331/28 (2006.01)
C09K 19/04 (2006.01)
C09K 19/18 (2006.01)

(52) U.S. Cl.
CPC ............ C09K 19/30 (2013.01); C07C 331/28 (2013.01); C09K 19/04 (2013.01); C09K 19/12 (2013.01); C09K 19/18 (2013.01); C09K 19/3059 (2013.01); C09K 2019/0444 (2013.01); C09K 2219/11 (2013.01)

(58) Field of Classification Search
None
See application file for complete search history.

(56) References Cited

U.S. PATENT DOCUMENTS

| 9,593,279 B2* | 3/2017 | Wittek | C09K 19/10 |
| 10,023,798 B2* | 7/2018 | Lapanik | C09K 19/12 |
| 2005/0012074 A1* | 1/2005 | Ban | C09K 19/0403 |
| | | | 252/299.63 |
| 2005/0067605 A1* | 3/2005 | Lussem | C09K 19/16 |
| | | | 252/299.01 |
| 2013/0342775 A1* | 12/2013 | Sun | C09K 19/42 |
| | | | 349/35 |
| 2016/0040066 A1 | 2/2016 | Wittek et al. | |
| 2017/0130129 A1 | 5/2017 | Wittek et al. | |

FOREIGN PATENT DOCUMENTS

| CN | 102352260 A * | 2/2012 |
| CN | 102433133 A * | 5/2012 |
| CN | 105985786 A * | 10/2016 |
| EP | 2982730 A1 | 2/2016 |
| WO | 2017137145 A1 | 8/2017 |

OTHER PUBLICATIONS

English translation of CN105985786. (Year: 2016).*
English translation of CN102433133. (Year: 2012).*
Reuter et al., "Highly birefringent, low-loss liquid crystals for terahertz applications", Jun. 25, 2013, APL Materials, 1, 012107-1 to 012107-7. (Year: 2013).*

(Continued)

Primary Examiner — Cynthia H Kelly
Assistant Examiner — Anna Malloy
(74) Attorney, Agent, or Firm — Millen White Zelano and Branigan, PC; Csaba Henter

(57) ABSTRACT

Liquid-crystalline media containing one or more compounds of formulae I-1, I-2 and/or I-3

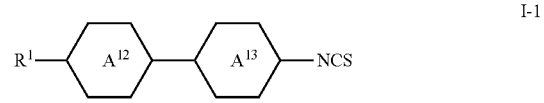

I-1

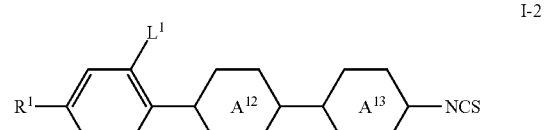

I-2

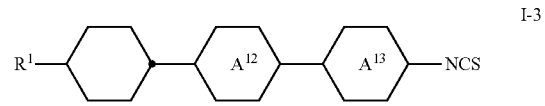

I-3 and one or more compounds of formulae II and/or III

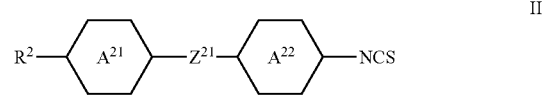

II

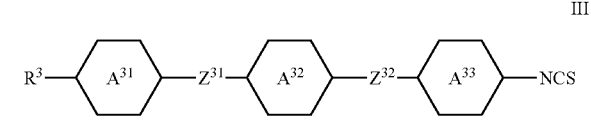

III and components containing these media for high-frequency technology, in particular phase shifters and microwave array antennas.

20 Claims, No Drawings

(56) References Cited

OTHER PUBLICATIONS

Mrukiewicz et al., "Dielectric Properties of Compounds Creating Dual-Frequency Nematic Liquid Crystals", 2013, vol. 124, 940-945. (Year: 2013).*
Reuter et al., "Terahertz and optical properties of nematic mixtures composed of liquid crystal isothiocyanates, fluorides and cyanides", 2013, Journal of Materials Chemistry C, 1, 4457-4463. (Year: 2013).*
Gauza et al., "Enhancing Birefringence by Doping Fluorinated Phenyltolanes", Dec. 2006, Journal of Display Technology, vol. 2 No. 4, 327-332. (Year: 2006).*
English translation of CN102352260. (Year: 2012).*
European Search Report for EP-17196558 dated Feb. 16, 2018.
Gauza, Sebastian et al., "Enhancing birefringence by doping fluorinated phenyltolanes," Journal of Display Technology, vol. 2, No. 4, Dec. 2006, pp. 327-332.

\* cited by examiner

LIQUID-CRYSTALLINE MEDIUM, COMPOUNDS, AND HIGH-FREQUENCY COMPONENTS

The present invention relates to liquid-crystalline media and to high-frequency components comprising same, especially microwave components for high-frequency devices, such as devices for shifting the phase of microwaves, in particular for microwave phased-array antennas.

Liquid-crystalline media have a been used for many years in electro-optical displays (liquid crystal displays: LCDs) in order to display information. More recently, however, liquid-crystalline media have also been proposed for use in components for microwave technology, such as, for example, in DE 10 2004 029 429.1 A and in JP 2005-120208 (A).

As a typical microwave application, the concept of the inverted microstrip line as described by K. C. Gupta, R. Garg, I. Bahl and P. Bhartia: Microstrip Lines and Slotlines, $2^{nd}$ ed., Artech House, Boston, 1996, is employed, for example, in D. Dolfi, M. Labeyrie, P. Joffre and J. P. Huignard: Liquid Crystal Microwave Phase Shifter. *Electronics Letters*, Vol. 29, No. 10, pp. 926-928, May 1993, N. Martin, N. Tentillier, P. Laurent, B. Splingart, F. Huert, Ph. Gelin, C. Legrand: Electrically Microwave Tunable Components Using Liquid Crystals. $32^{nd}$ European Microwave Conference, pp. 393-396, Milan 2002, or in Weil, C.: Passiv steuerbare Mikrowellenphasenschieber auf der Basis nichtlinearer Dielektrika [Passively Controllable Microwave Phase Shifters based on Nonlinear Dielectrics], Darmstädter Dissertationen D17, 2002, C. Weil, G. Lüssem, and R. Jakoby: Tunable Invert-Microstrip Phase Shifter Device Using Nematic Liquid Crystals, *IEEE MTT-S Int. Microw. Symp.*, Seattle, Wash., June 2002, pp. 367-370, together with the commercial liquid crystal K15 from Merck KGaA. C. Weil, G. Lüssem, and R. Jakoby: Tunable Invert-Microstrip Phase Shifter Device Using Nematic Liquid Crystals, *IEEE MTT-S Int. Microw. Symp.*, Seattle, Wash., June 2002, pp. 367-370, achieve phase shifter qualities of 12°/dB at 10 GHz with a control voltage of about 40 V therewith. The insertion losses of the LC, i.e. the losses caused only by the polarisation losses in the liquid crystal, are given as approximately 1 to 2 dB at 10 GHz in Weil, C.: Passiv steuerbare Mikrowellenphasenschieber auf der Basis nichtlinearer Dielektrika [Passively Controllable Microwave Phase Shifters based on Nonlinear Dielectrics], Darmstädter Dissertationen D17, 2002. In addition, it has been determined that the phase shifter losses are determined primarily by the dielectric LC losses and the losses at the waveguide junctions. T. Kuki, H. Fujikake, H. Kamoda and T. Nomoto: Microwave Variable Delay Line Using a Membrane Impregnated with Liquid Crystal. *IEEE MTT-S Int. Microwave Symp. Dig.* 2002, pp. 363-366, June 2002, and T. Kuki, H. Fujikake, T. Nomoto: Microwave Variable Delay Line Using Dual-Frequency Switching-Mode Liquid Crystal. *IEEE Trans. Microwave Theory Tech.*, Vol. 50, No. 11, pp. 2604-2609, November 2002, also address the use of polymerised LC films and dual-frequency switching-mode liquid crystals in combination with planar phase shifter arrangements.

A. Penirschke, S. Müller, P. Scheele, C. Weil, M. Wittek, C. Hock and R. Jakoby: "Cavity Perturbation Method for Characterization of Liquid Crystals up to 35 GHz", $34^{th}$ European Microwave Conference—Amsterdam, pp. 545-548 describe, inter alia, the properties of the known single liquid-crystalline substance K15 (Merck KGaA, Germany) at a frequency of 9 GHz.

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (likewise Merck KGaA, Germany).

DE 10 2004 029 429.1 A describes the use of liquid-crystal media in microwave technology, inter alia in phase shifters. It has already investigated liquid-crystalline media with respect to their properties in the corresponding frequency range. In addition, it describes liquid-crystalline media which comprise a small amount of a single compound of the formula

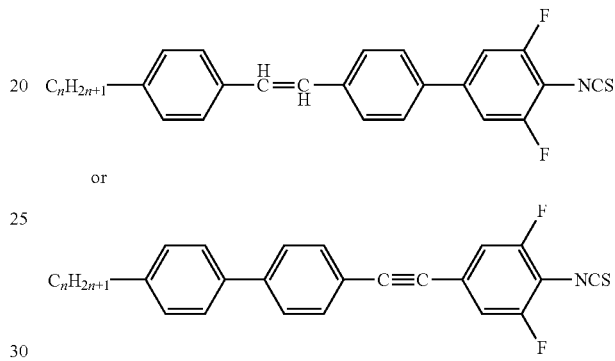

or in combination with the well known cyanobiphenyl compound

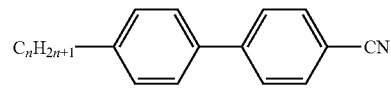

and also media comprising, inter alia, compounds of the following structures:

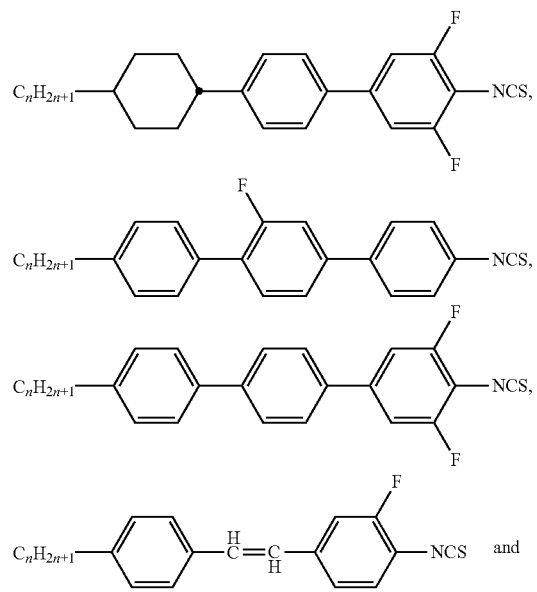

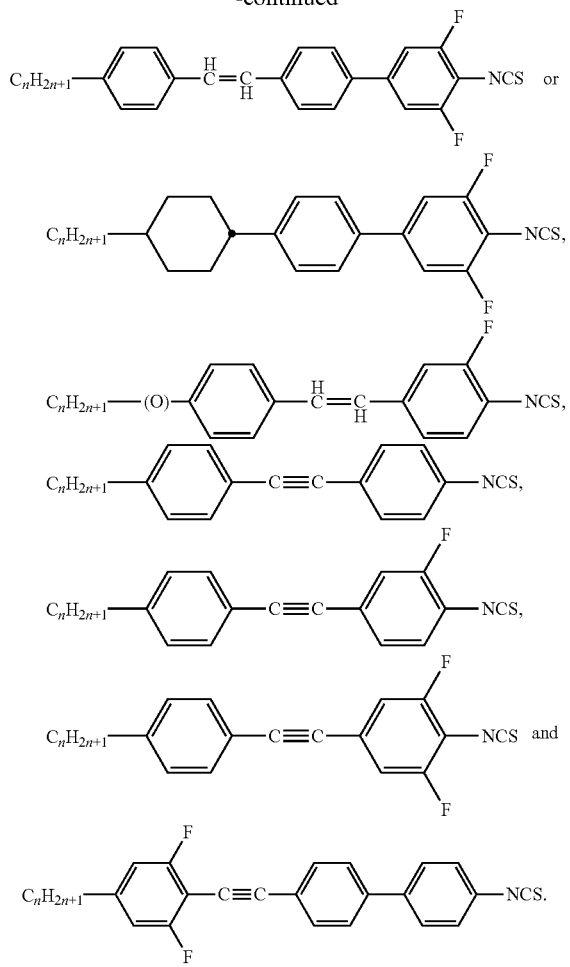

However, these compositions are all afflicted with several more or less serious disadvantages. Most of them result, besides other deficiencies, in disadvantageously high losses and/or inadequate phase shifts or inadequate material quality. These relatively simple mixtures show limited performance for the application in devices operating in the microwave regime and even need to be significantly improved with respect to their general physical properties, such as, especially, the clearing point, the phase range, especially their stability against storage at low temperatures, and their viscosities, in particular their rotational viscosity.

The known devices for the high frequency-technology comprising these media do still lack sufficient stability and, in particular, fast response.

For these applications, liquid-crystalline media having particular, hitherto rather unusual and uncommon properties or combinations of properties are required.

Novel liquid-crystalline media having improved properties are thus necessary. In particular, the dielectric loss in the microwave region must be reduced and the material quality ($\eta$, sometimes also called figure of merit, short FoM), i.e. a high tunability and, at the same time, a low dielectric loss, must be improved. Besides these requirements increased focus has to be placed on improved response times for several envisaged applications especially for those devices using planar structures such as e.g. phase shifters and leaky antennas.

In addition, there is a steady demand for an improvement in the low-temperature behaviour of the components. Both an improvement in the operating properties at low temperatures and also in the shelf life are necessary here.

Therefore, there is a considerable demand for liquid-crystalline media having suitable properties for corresponding practical applications.

Liquid crystal mixtures based on isothiocyanate compounds are disclosed in EP 2 982 730 A1. However, mixtures proposed therein all comprise compounds having unsaturated linking groups such as —CH=CH— (stilbenes) or —C≡C— (tolanes), some of which can be difficult to synthesise or can be comparatively sensitive to stress under extreme conditions, as for example when exposed to UV-light, heat or upon storage at low temperatures.

It is another aim of the present invention to avoid the use of stilbene or tolane derivatives and also to simplify the mixture production by reducing the number of different compounds used.

Surprisingly, it has been found that it is possible to achieve liquid-crystalline media having a suitably fast switching times, a suitable, nematic phase range, high tunability and low loss, which do not have the disadvantages of the prior-art materials, or at least only do so to a considerably reduced extent, by using high concentrations of compounds of formula I below.

The present invention relates to liquid-crystalline media comprising one or more compounds of formula I

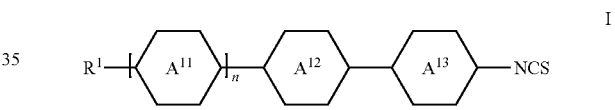

in which
$R^1$ denotes H, unfluorinated alkyl or unfluorinated alkoxy having 1 to 17, preferably having 3 to 10, C atoms or unfluorinated alkenyl, unfluorinated alkenyloxy or unfluorinated alkoxyalkyl having 2 to 15, preferably 3 to 10, C atoms, preferably unfluorinated alkyl or unfluorinated alkenyl, n is 0, 1 or 2,

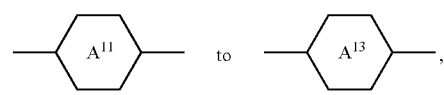

on each occurrence, independently of one another, denote

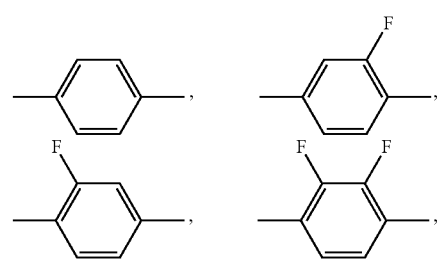

-continued
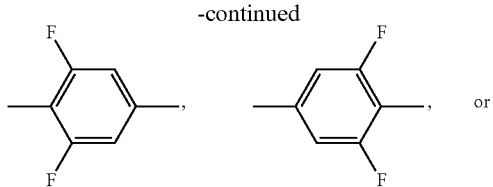 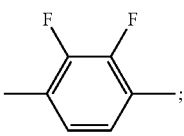 or
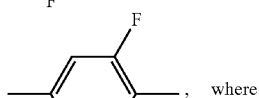, where
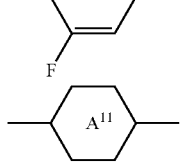
alternatively denotes
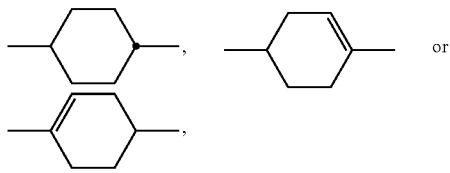
preferably
,
and in case n=2, one of
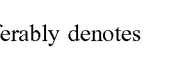
preferably denotes
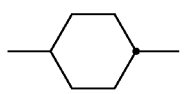
and the other preferably denotes
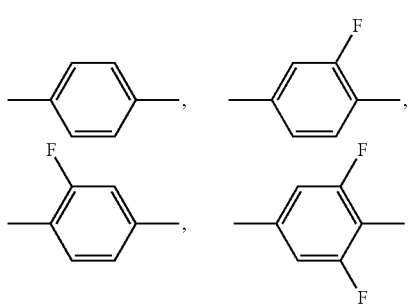 or
-continued
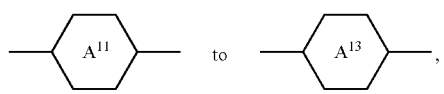;
preferably
 to ,
independently of one another, denote
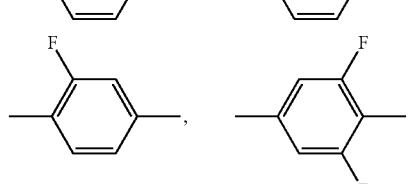
more preferably
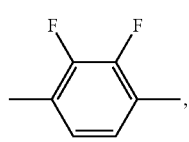
denotes
 or ,
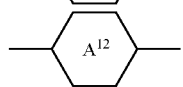
denotes
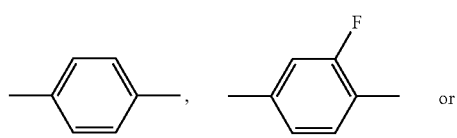 or

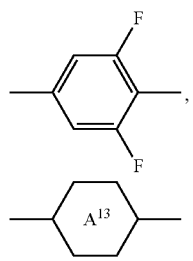

denotes

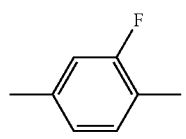 or 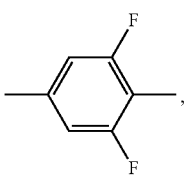, and where the total concentration of compounds of formula I is 73% by weight or more.

In a preferred embodiment of the present invention, the compounds of formula I are selected from the group of compounds of the formulae I-1 to I-5:

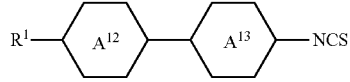 I-1

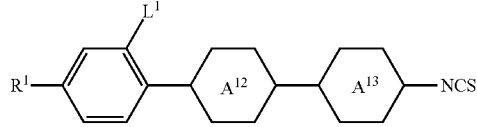 I-2

 I-3

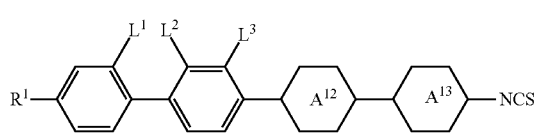 I-4

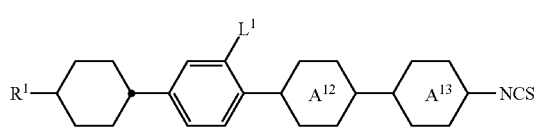 I-5 in which
$L^1$, $L^2$ and $L^3$ on each occurrence, identically or differently, denote H or F,
and the other groups have the respective meanings indicated above for formula I and preferably
$R^1$ denotes unfluorinated alkyl having 1 to 7 C atoms or unfluorinated alkenyl having 2 to 7 C atoms.

The media preferably comprise one or more compounds of formula I-1, which are preferably selected from the group of the compounds of the formulae I-1a to I-1d, preferably of formula I-1 b:

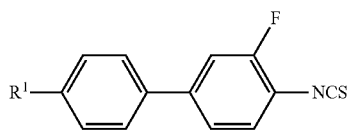 I-1a

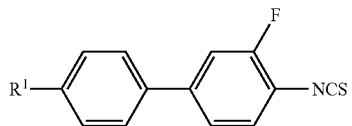 I-1b

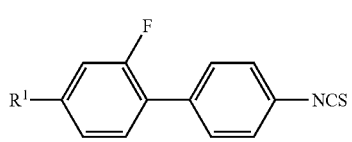 I-1c

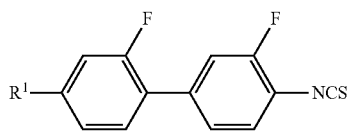 I-1d in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula I-2, which are preferably selected from the group of the compounds of the formulae I-2a to I-2e, preferably of formula I-2c:

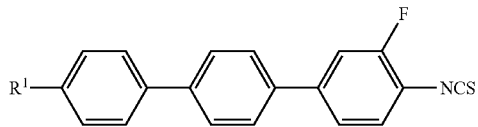 I-2a

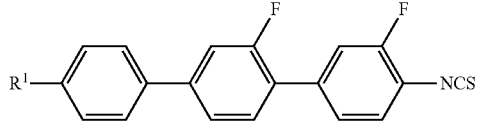 I-2b

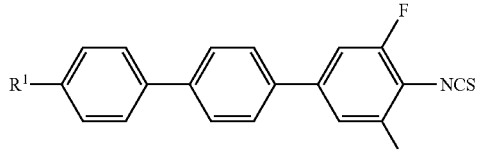 I-2c

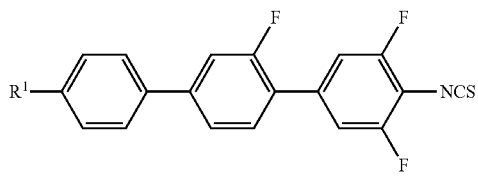 I-2d

I-2e

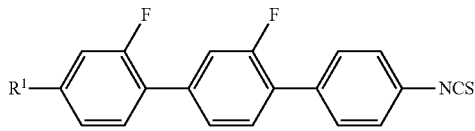

in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-3, which are preferably selected from the group of the compounds of the formulae I-3a to I-3d, particularly preferably of formula I-3b:

I-3a

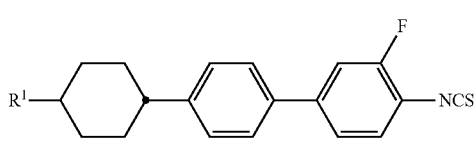

I-3b

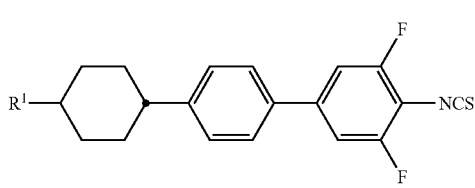

I-3c

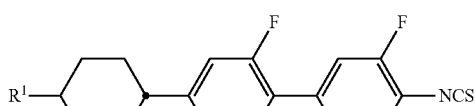

I-3d

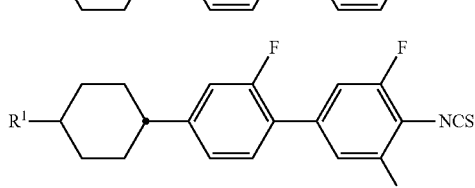

in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-4, which are preferably selected from the group of the compounds of the formulae I-4a to I-4d, particularly preferably of formula I-4b:

I-4a

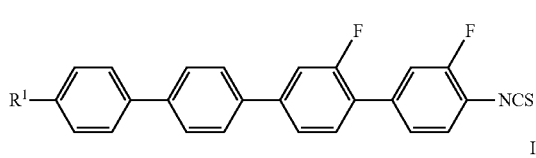

I-4b

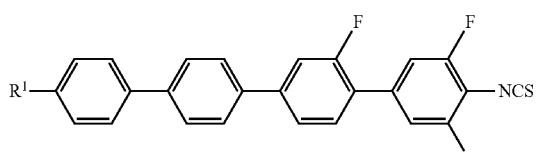

I-4c

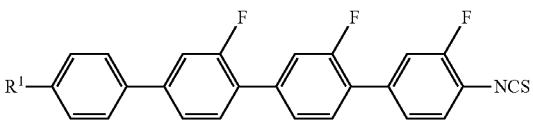

I-4d

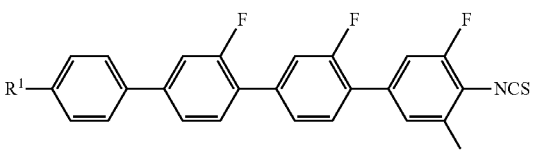

I-4e

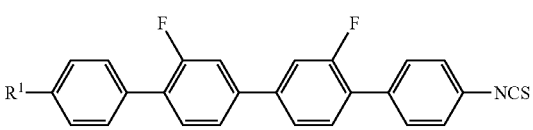

in which R¹ has the meaning indicated above for formula I and preferably denotes unfluorinated alkyl having 1 to 7 C atoms or unfluorinated alkenyl having 2 to 7 C atoms.

The media preferably comprise one or more compounds of formula I-5, which are preferably selected from the group of the compounds of the formulae I-5a to I-5d, particularly preferably of formula I-5b:

I-5a

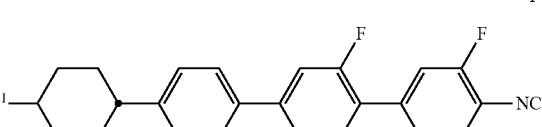

I-5b

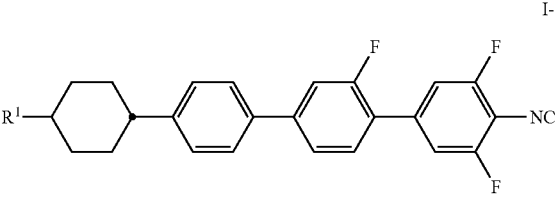

I-5c

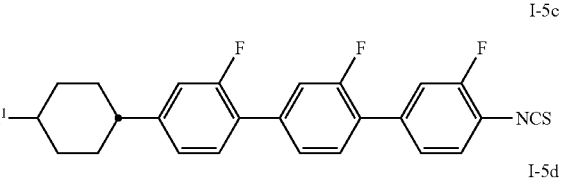

I-5d

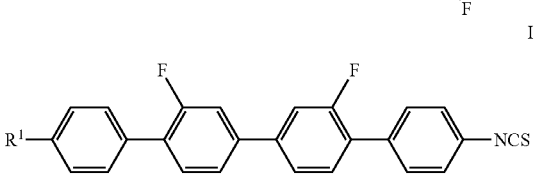

in which R¹ has the meaning indicated above for formula I and preferably denotes unfluorinated alkyl having 1 to 7 C atoms or unfluorinated alkenyl having 2 to 7 C atoms.

Additionally, the liquid-crystalline media according to the present invention in a certain embodiment preferably comprise one or more compounds selected from the group of compounds of formulae II and III,

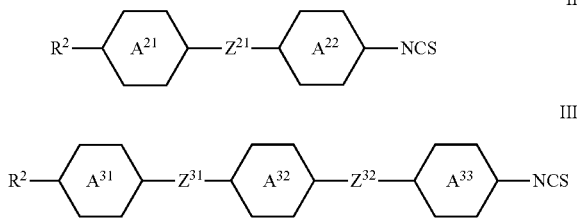

in which

R² denotes H, unfluorinated alkyl or unfluorinated alkoxy having 1 to 17, preferably having 3 to 10, C atoms or unfluorinated alkenyl, unfluorinated alkenyloxy or unfluorinated alkoxyalkyl having 2 to 15, preferably 3 to 10, C atoms, preferably unfluorinated alkyl or unfluorinated alkenyl, Z²¹ denotes trans-CH=CH—, trans-CF=CF— or —C≡C—, preferably —C≡C— or trans-CH=CH—, and

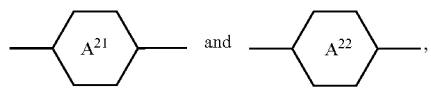

independently of one another, denote

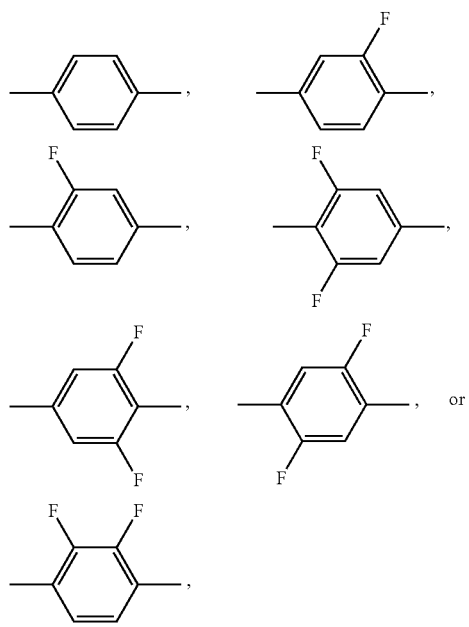

preferably

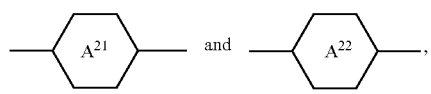

independently of one another, denote

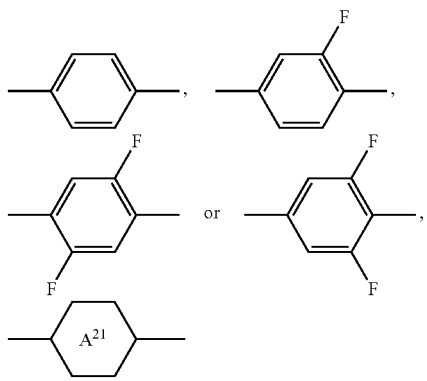

preferably denotes

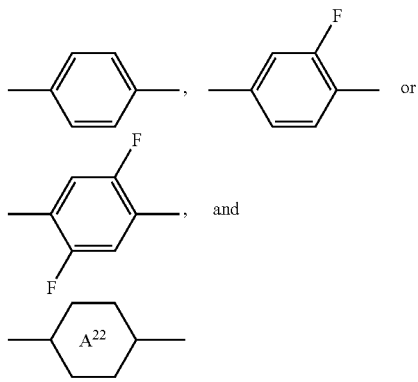

preferably denotes

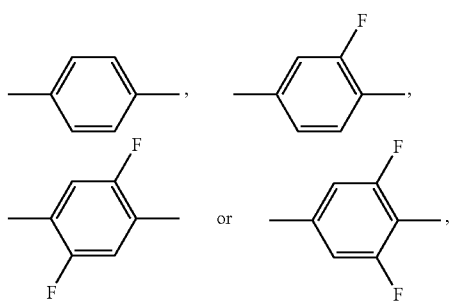

more preferably

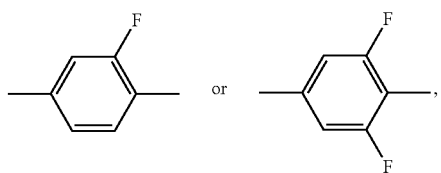

and in which

R³ denotes H, unfluorinated alkyl or unfluorinated alkoxy having 1 to 17, preferably having 3 to 10, C atoms or unfluorinated alkenyl, unfluorinated alkenyloxy or unfluorinated alkoxyalkyl having 2 to 15, preferably 3 to 10, C atoms, preferably unfluorinated alkyl or unfluorinated alkenyl, one of $Z^{31}$ and $Z^{32}$, preferably $Z^{32}$, denotes trans-CH=CH—, trans-CF=CF— or —C≡C— and the other one, independently thereof, denotes trans-CH=CH—, trans-CF=CF— or a single bond, preferably one of them, preferably $Z^{32}$; denotes —C≡C— or trans-CH=CH— and the other denotes a single bond, and

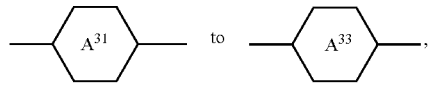

independently of one another, denote

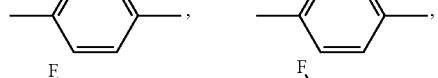

alternatively independently denotes

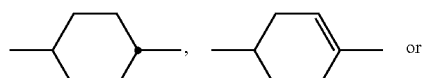

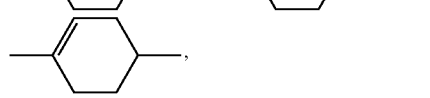

preferably

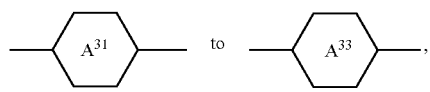

independently of one another, denote

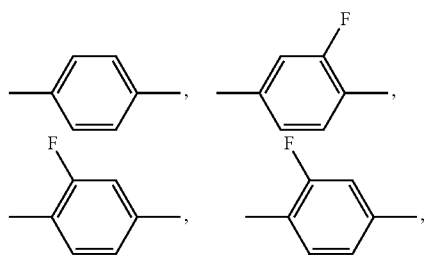

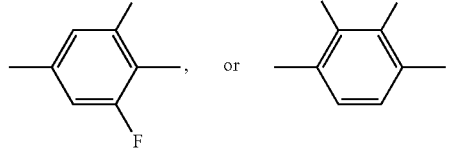

more preferably

denotes

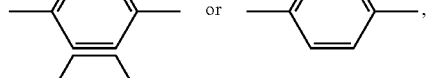

denotes

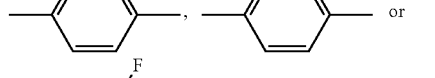

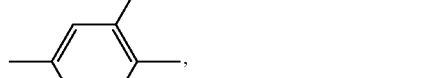

and
more preferably

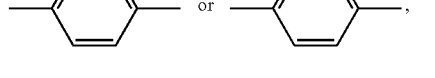

-continued
denotes
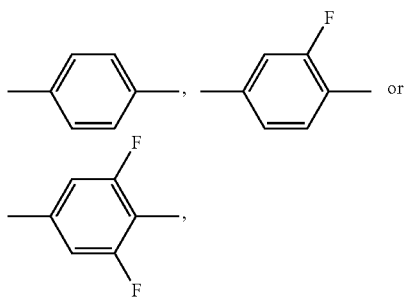
more preferably
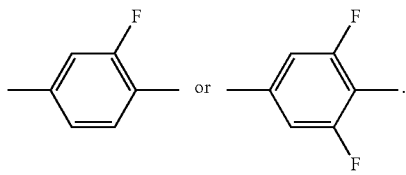
Additionally, the liquid-crystalline media according to the present invention in a certain embodiment, which may be the same or different from the previous preferred embodiment, preferably comprise one or more compounds of formula IV,
IV
in which
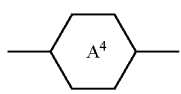
denotes
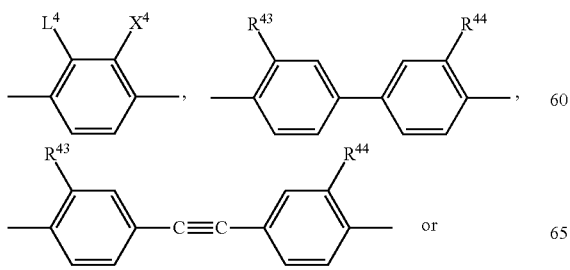
-continued
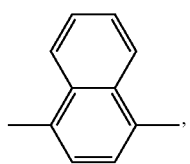
preferably
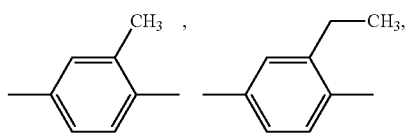
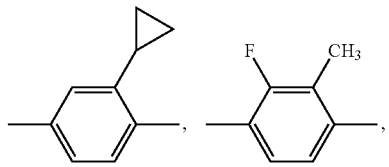
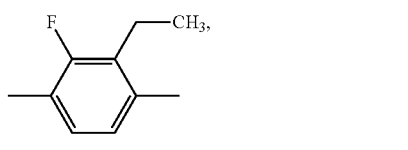
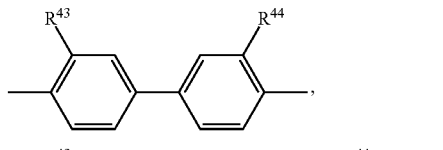
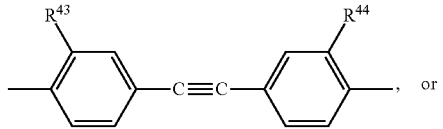
particularly preferably
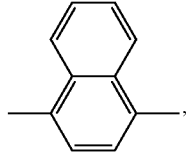
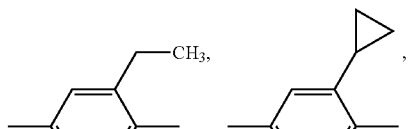
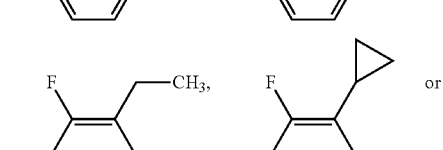
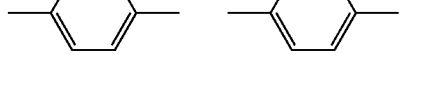

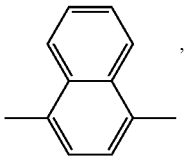

L$^4$ denotes alkyl having 1 to 6 C atoms, cycloalkyl having 3 to 6 C atoms or cycloalkenyl having 4 to 6 C atoms, preferably CH$_3$, C$_2$H$_5$, n-C$_3$H$_7$ (—(CH$_2$)$_2$CH$_3$), i-C$_3$H$_7$ (—CH(CH$_3$)$_2$), cyclopropyl, cyclobutyl, cyclohexyl, cyclopent-1-enyl or cyclohex-1-enyl, and particularly preferably CH$_3$, C$_2$H$_5$, cyclopropyl or cyclobutyl, X$^4$ denotes H, alkyl having 1 to 3 C atoms or halogen, preferably H, F or Cl, and particularly preferably H or F and very particularly preferably F, R$^{41}$ to R$^{44}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkylalkyl or alkylcycloalkenylalkyl, each having up to 15 C atoms, and alternatively one of R$^{43}$ and R$^{44}$ or both also denote H, preferably R$^{41}$ and R$^{42}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 7 C atoms, particularly preferably R$^{41}$ denotes unfluorinated alkyl having 1 to 7 C atoms or unfluorinated alkenyl, unfluorinated alkenyloxy or unfluorinated alkoxyalkyl, each having 2 to 7 C atoms, and particularly preferably R$^{42}$ denotes unfluorinated alkyl or unfluorinated alkoxy, each having 1 to 7 C atoms, and preferably R$^{43}$ and R$^{44}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of R$^{43}$ and R$^{44}$ denotes n-alkyl, particularly preferably methyl, ethyl or n-propyl, and the other denotes H or n-alkyl, particularly preferably H, methyl, ethyl or n-propyl.

In a preferred embodiment the liquid crystal medium according to the invention comprises one or more chiral compounds.

In a preferred embodiment the liquid crystal medium according to the invention comprises one or more chiral compounds selected from the group of compounds of formulae A-I to A-III:

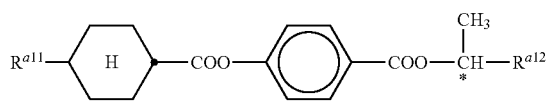

A-I

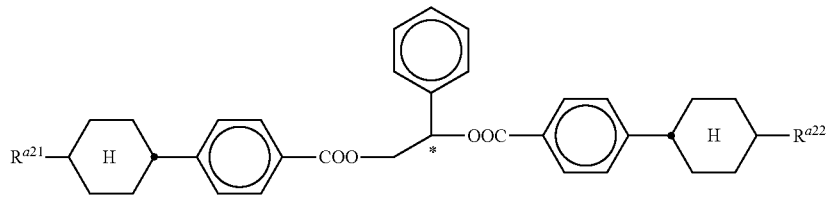

A-II

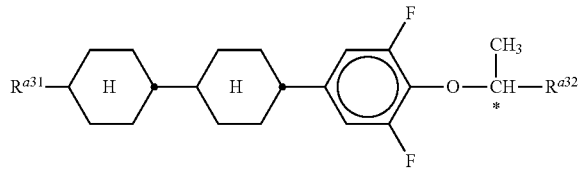

A-III in which

R$^{a11}$ and R$^{a12}$, independently of one another, are alkyl, oxaalkyl or alkenyl having from 2 to 9, preferably up to 7, carbon atoms, and R$^{a11}$ is alternatively methyl or alkoxy having from 1 to 9 carbon atoms, preferably both are alkyl, preferably n-alkyl, R$^{a21}$ and R$^{a22}$, independently of one another, are alkyl or alkoxy having from 1 to 9, preferably up to 7, carbon atoms, oxaalkyl, alkenyl or alkenyloxy having from 2 to 9, preferably up to 7, carbon atoms, preferably both are alkyl, preferably n-alkyl, R$^{a31}$ and R$^{a32}$, independently of one another, are alkyl, oxaalkyl or alkenyl having from 2 to 9, preferably up to 7, carbon atoms, and R$^{a11}$ is alternatively methyl or alkoxy having from 1 to 9 carbon atoms, preferably both are alkyl, preferably n-alkyl.

Particular preference is given to dopants selected from the group consisting of the compounds of the following formulae:

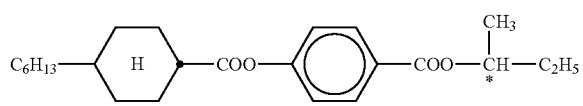

A-I-1

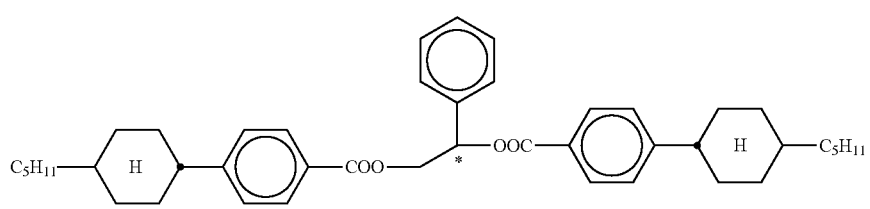

A-II-1

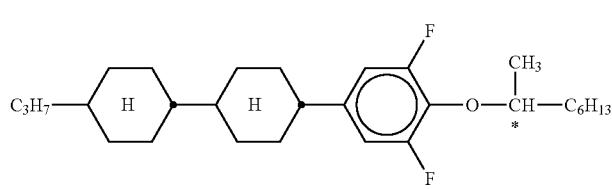

A-III-1

Further preferred chiral compounds are derivatives of the isosorbide, isomannitol or isoiditol of the following formula A-IV:

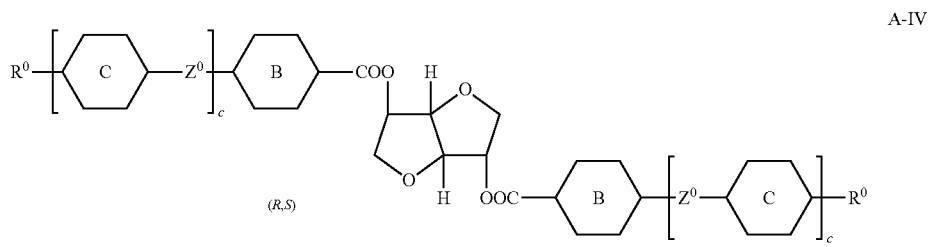

A-IV in which the group is

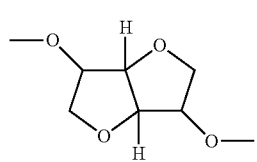

(dianhydrosorbitol)

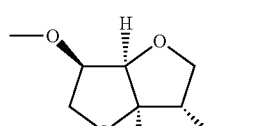

(dianhydrosorbitol)

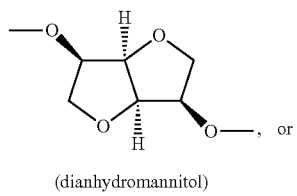
, or (dianhydromannitol)

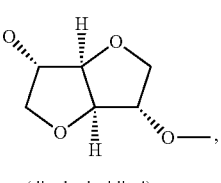
, (dianhydroiditol)

preferably dianhydrosorbitol, and chiral ethanediol derivatives, such as, for example, diphenylethanediol (hydrobenzoin), in particular mesogenic hydrobenzoin derivatives of the following formula A-V:

A-V

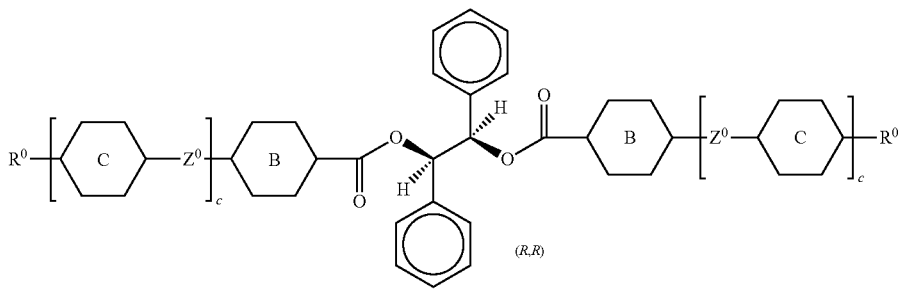

(R,R)

including the (R,S), (S,R), (R,R) and (S,S) enantiomers, which are not shown,
in which

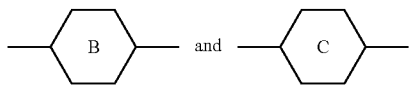

are each, independently of one another, 1,4-phenylene, which may also be mono-, di- or trisubstituted by L, or 1,4-cyclohexylene,
L is H, F, Cl, CN or optionally halogenated alkyl, alkoxy, alkylcarbonyl, alkoxycarbonyl or alkoxycarbonyloxy having 1-7 carbon atoms,
c is 0 or 1,
$Z^0$ is —COO—, —OCO—, —$CH_2CH_2$— or a single bond, and
$R^0$ is alkyl, alkoxy, alkylcarbonyl, alkoxycarbonyl or alkylcarbonyloxy having 1-12 carbon atoms.

The compounds of the formula A-IV are described in WO 98/00428. The compounds of the formula A-V are described in GB-A-2,328,207.

Very particularly preferred dopants are chiral binaphthyl derivatives, as described in WO 02/94805, chiral binaphthol acetal derivatives, as described in WO 02/34739, chiral TADDOL derivatives, as described in WO 02/06265, and chiral dopants having at least one fluorinated bridging group and a terminal or central chiral group, as described in WO 02/06196 and WO 02/06195.

Particular preference is given to chiral compounds of the formula A-VI

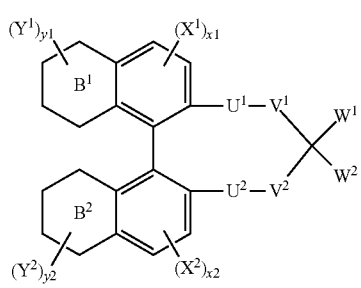

A-VI in which
$X^1$, $X^2$, $Y^1$ and $Y^2$ are each, independently of one another, F, Cl, Br, I, CN, SCN, $SF_5$, straight-chain or branched alkyl having from 1 to 25 carbon atoms, which may be monosubstituted or polysubstituted by F, Cl, Br, I or CN and in which, in addition, one or more non-adjacent $CH_2$ groups may each, independently of one another, be replaced by —O—, —S—, —NH—, $NR^0$—, —CO—, —COO—, —OCO—, —OCOO—, —S—CO—, —CO—S—, —CH=CH— or —C≡C— in such a way that O and/or S atoms are not bonded directly to one another, a polymerisable group or cycloalkyl or aryl having up to 20 carbon atoms, which may optionally be monosubstituted or polysubstituted by halogen, preferably F, or by a polymerisable group,
$x^1$ and $x^2$ are each, independently of one another, 0, 1 or 2,
$y^1$ and $y^2$ are each, independently of one another, 0, 1, 2, 3 or 4,
$B^1$ and $B^2$ are each, independently of one another, an aromatic or partially or fully saturated aliphatic six-membered ring in which one or more CH groups may be replaced by N atoms and one or more non-adjacent $CH_2$ groups may be replaced by O and/or S,
$W^1$ and $W^2$ are each, independently of one another, —$Z^1$-$A^1$-$(Z^2$-$A^2)_m$-R, and one of the two is alternatively $R^1$ or $A^3$, but both are not simultaneously H, or

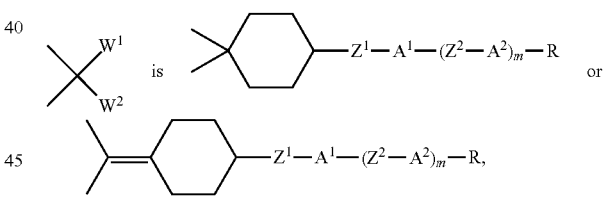

$U^1$ and $U^2$ are each, independently of one another, $CH_2$, O, S, CO or CS,
$V^1$ and $V^2$ are each, independently of one another, $(CH_2)_n$, in which from one to four non-adjacent $CH_2$ groups may be replaced by O and/or S, and one of $V^1$ and $V^2$ and, in the case where

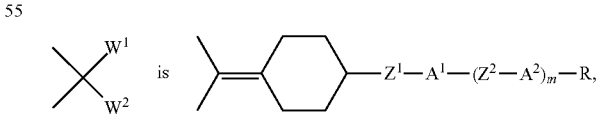

both are a single bond,
$Z^1$ and $Z^2$ are each, independently of one another, —O—, —S—, —CO—, —COO—, —OCO—, —O—COO—, —CO—$NR^0$—, —$NR^0$—CO—, —O—$CH_2$—, —$CH_2$—O—, —S—$CH_2$—, —$CH_2$—S—, —$CF_2$—O—, —O—$CF_2$—, —$CF_2$—S—, —S—$CF_2$—, —$CH_2$—$CH_2$—, —$CF_2$—$CH_2$—, —$CH_2$—$CF_2$—, —$CF_2$—

CF$_2$—, —CH=N—, —N=CH—, —N=N—, —CH=CH—, —CF=CH—, —CH=CF—, —CF=CF—, —C≡C—, a combination of two of these groups, where no two O and/or S and/or N atoms are bonded directly to one another, preferably —CH=CH—COO—, or —COO—CH=CH—, or a single bond, $A^1$, $A^2$ and $A^3$ are each, independently of one another, 1,4-phenylene, in which one or two non-adjacent CH groups may be replaced by N, 1,4-cyclohexylene, in which one or two non-adjacent CH$_2$ groups may be replaced by O and/or S, 1,3-dioxolane-4,5-diyl, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where each of these groups may be monosubstituted or polysubstituted by L, and in addition $A^1$ is a single bond, L is a halogen atom, preferably F, CN, NO$_2$, alkyl, alkoxy, alkylcarbonyl, alkoxycarbonyl or alkoxycarbonyloxy having 1-7 carbon atoms, in which one or more H atoms may be replaced by F or Cl, m is in each case, independently, 0, 1, 2 or 3, and R and $R^1$ are each, independently of one another, H, F, Cl, Br, I, CN, SCN, SF$_5$, straight-chain or branched alkyl having from 1 or 3 to 25 carbon atoms respectively, which may optionally be monosubstituted or polysubstituted by F, Cl, Br, I or CN, and in which one or more non-adjacent CH$_2$ groups may be replaced by —O—, —S—, —NH—, —NR$^0$—, —CO—, —COO—, —OCO—, —O—COO—, —S—CO—, —CO—S—, —CH=CH— or —C≡C—, where no two O and/or S atoms are bonded directly to one another, or a polymerisable group.

Particular preference is given to chiral binaphthyl derivatives of the formula A-VI-1

A-VI-1

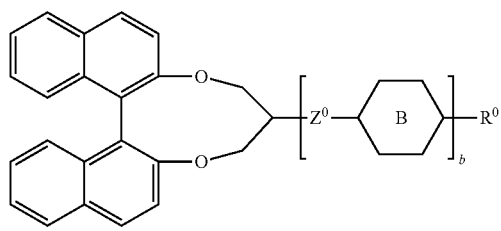

in particular those selected from the following formulae A-VI-1a to A-VI-1c:

A-VI-1a

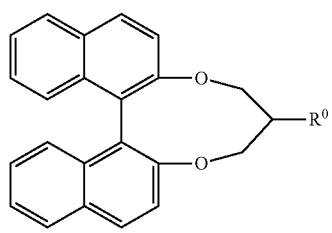

A-VI-1b

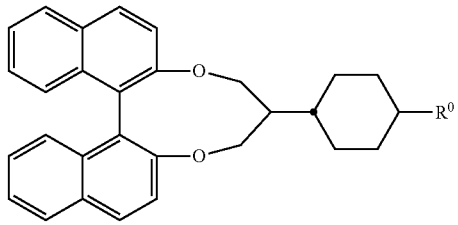

A-VI-1c

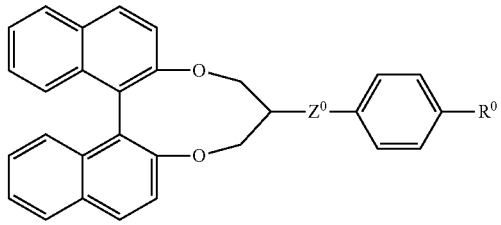

in which ring B and $Z^0$ are as defined for the formula A-IV, and $R^0$ as defined for formula A-IV or H or alkyl having from 1 to 4 carbon atoms, and b is 0, 1 or 2, and $Z^0$ is, in particular, —OCO— or a single bond.

Particular p reference is furthermore given to chiral binaphthyl derivatives of the formula A-VI-2

A-VI-2

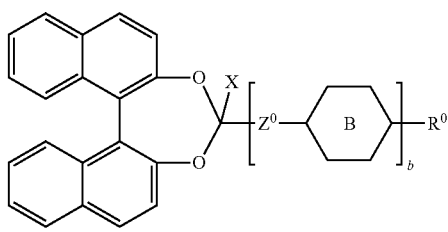

in particular those selected from the following formulae A-VI-2a to A-VI-2f:

A-VI-2a

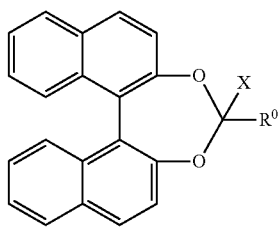

A-VI-2b

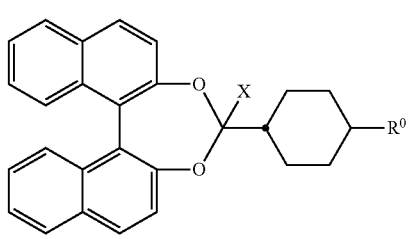

-continued

A-VI-2c

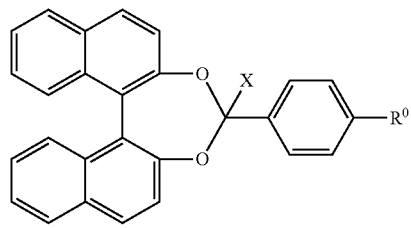

A-VI-2d

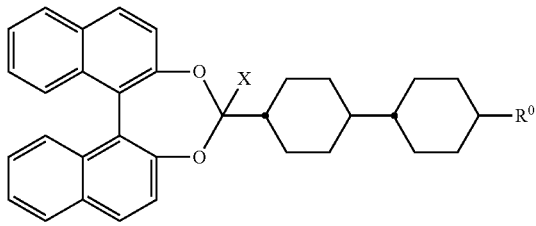

A-VI-2e

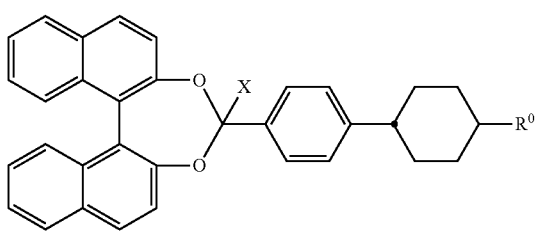

A-VI-2f

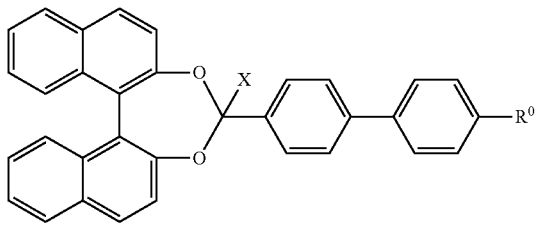

in which $R^0$ is as defined for the formula A-VI, and X is H, F, Cl, CN or $R^0$ preferably F.

The present invention further relates to compounds of formula I above, wherein n is 2.

The compounds according to the present invention can be synthesized by or in analogy to known methods described in the literature (for example in the standard works such as Houben-Weyl, Methoden der Organischen Chemie [Methods of Organic Chemistry], Georg-Thieme-Verlag, Stuttgart), under reaction conditions which are known and suitable for said reactions. Use may also be made here of variants which are known per se, but are not mentioned here. In particular, they can be prepared as described in or in analogy to the following reaction schemes. Further methods for preparing the inventive compounds can be taken from the examples.

Preferably, the isothiocyanate group is introduced in the last step of the synthesis of compounds of formula I by reaction of an aniline (1) with for example 1,1-thiocarbonyl diimidazole (2), as shown in scheme 1.

Scheme 1

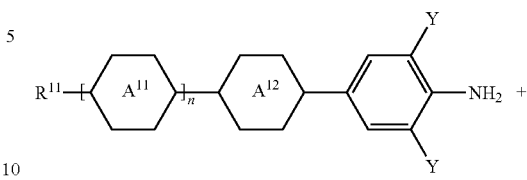

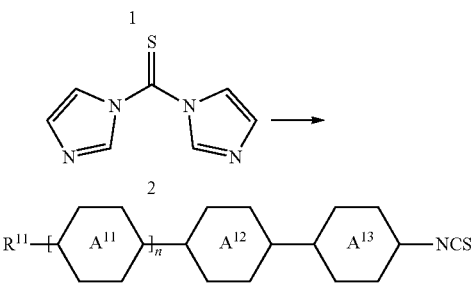

In scheme 1, the occurring groups and parameters have the meaning as indicated above for formula I and Y denotes H or F.

A preferred synthesis of compounds of the intermediates 1 is shown in scheme 2 where commercially available p-aminoboronic acids or esters (4) are coupled in a Suzuki coupling with the corresponding reactants (3). The reactants 3 are known from the literature and described in e.g. CN 104478768 A and CN 102399117 A or can be synthesised in an analogous fashion.

Scheme 2.

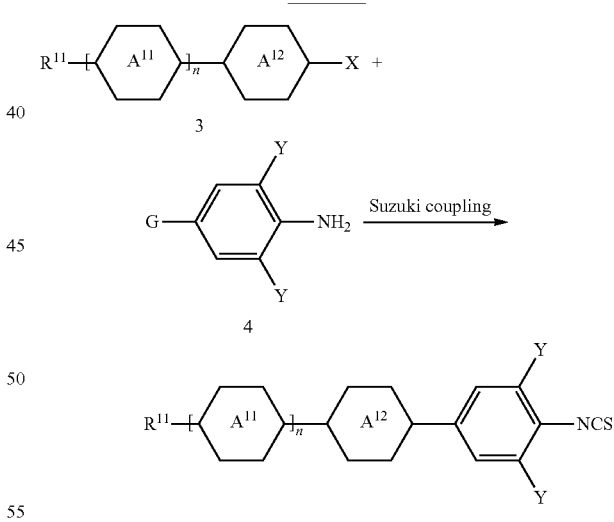

In scheme 2, the occurring groups and parameters have the meaning as indicated above for formula I and Y denotes H or F, X denotes Cl, Br, I, or triflate and G denotes a boronic acid or ester group.

The liquid-crystalline media in accordance with the present invention preferably comprise, more preferably predominantly consist of, even more preferably essentially consist of and very preferably completely consist of compounds selected from the compounds of the formula I.

In a preferred embodiment of the present invention the liquid-crystalline media predominantly consist of, more preferably essentially consist of, and, most preferably completely consist of isothiocyanate compounds, preferably selected from the group of the compounds of the formula I In this application, "comprise" in connection with compositions means that the entity in question, i.e. the medium or the component, comprises the component or components or compound or compounds indicated, preferably in a total concentration of 10% or more and very preferably 20% or more. The expression "predominantly consist of" means that the entity in question comprises 55% or more, preferably 60% or more and very preferably 70% or more of the component or components or compound or compounds indicated. The expression "essentially consist of" means that the entity in question comprises 80% or more, preferably 90% or more and very preferably 95% or more of the component or components or compound or compounds indicated. The expression "completely consist of" means that the entity in question comprises 98% or more, preferably 99% or more and very preferably 100.0% of the component or components or compound or compounds indicated.

Other mesogenic compounds which are not explicitly mentioned above can optionally and advantageously also be used in the media in accordance with the present invention. Such compounds are known to the person skilled in the art.

The liquid-crystalline media in accordance with the present application preferably comprise in total 73% to 100%, preferably 75% to 95% and particularly preferably 80% to 90%, of compounds of formula I.

The liquid-crystalline media in accordance with the present application preferably comprise in total 73% or more, preferably 80% or more and particularly preferably 90% or more compounds of formula I.

The liquid-crystalline media in accordance with the present application preferably comprise in total 73% or more, preferably 80% or more particularly preferably 90% or more compounds selected from the group of compounds of formulae I-1, I-2 and I-3.

In a preferred embodiment of the present invention the medium completely consists of compounds of formula I.

In a preferred embodiment, the total concentration of the compounds of formula I-1 in the media according to the present invention is in the range from 5% to 40%, more preferably from 10% to 30%, still more preferably from 15% to 27% and particularly preferably from 19% to 25%.

The compounds of formula I-1 are preferably selected from compounds of the formula I-1 b.

In a preferred embodiment, the total concentration of the compounds of formula I-2 in the media according to the present invention is in the range from 15% to 55%, more preferably from 20% to 45%, and particularly preferably from 25% to 40%.

In a preferred embodiment, the total concentration of the compounds of formula I-3 in the media according to the present invention is in the range from 20% to 60%, more preferably from 30% to 55%, and particularly preferably from 40% to 50%.

In a preferred embodiment, the total concentration of the compounds of formula I-3 in the media according to the present invention is 41% or more, more preferably 45% or more and particularly preferably 50% or more.

In a preferred embodiment of the present invention the total concentration of the compounds of formula I-3b in the media is in the range of 10% to 45%, more preferably from 15% to 35%, and particularly preferably from 25% to 30%.

In a preferred embodiment of the present invention the medium comprises a compound of formula I-1 b in a total concentration of 19% or more.

In a preferred embodiment of the present invention the medium comprises one or more compounds selected from the group of compounds of formulae II and III in a total concentration of 0.1% to 29%, preferably up to 27%, more preferably 2% to 20%, particularly preferably 3% to 10% of the mixture as a whole.

In a preferred embodiment of the present invention the medium comprises no compounds selected from the group of compounds of formulae II and III.

In a preferred embodiment of the present invention the medium completely consists of compounds of formula I.

In another preferred embodiment of the present invention, the medium comprises two or more compounds selected from the group of compounds of the formulae formula I and II and/or III.

In another preferred embodiment the medium according to the present invention comprises two or more compounds selected from the group of compounds of the formulae I and IV.

In yet another preferred embodiment the medium according to the present invention comprises two or more compounds selected from the group of compounds of the formulae I and IV and II and/or III.

The medium according to the invention preferably comprises four or more compounds of formula I. Preferably, the medium comprises one or more compounds of formula I-1 and one or more compounds of formula I-2 and one or more compounds of formula I-3.

In a preferred embodiment of the present invention the medium comprises one or more compounds selected from the group of compounds of formulae I-1, I-2 and I-3 and one or more compounds selected from the group of compounds of formulae I-4 and I-5.

Further preferred embodiments are as follows (the definitions of the abbreviations (acronyms) are indicated below in Table D or are evident from Tables A to C):

- the medium comprises one or more compounds of formula GGP-n-S in a total concentration of 9% by weight or more;
- the medium comprises one or more compounds of formula PGG-n-S in a total concentration of 13% by weight or more;
- the medium comprises one or more compounds of formula PGU-n-S in a total concentration of 25% by weight or more;
- the medium comprises one or more compounds of formula CPU-n-S;
- the medium comprises one or more compounds of formula CGU-n-S in a total concentration of 41% by weight or more;
- the medium comprises two or more homologues of compounds of the formula PGU-n-S.

The liquid-crystal media in accordance with the present invention preferably have a clearing point of 90° C. or more, more preferably 100° C. or more, even more preferably 120° C. or more, particularly preferably 150° C. or more and very particularly preferably 170° C. or more.

The liquid-crystal media in accordance with the present invention preferably have a clearing point of 160° C. or less, more preferably 140° C. or less, particularly preferably 120° C. or less, and very particularly preferably 100° C. or less.

The nematic phase of the media according to the invention preferably extends at least from 0° C. or less to 90° C. or more. It is advantageous for the media according to the invention to exhibit even broader nematic phase ranges, preferably at least from −10° C. or less to 120° C. or more, very preferably at least from −20° C. or less to 140° C. or more and in particular at least from −30° C. or less to 150° C. or more, very particularly preferably at least from −40° C. or less to 170° C. or more.

The Δε of the liquid-crystal medium according to the present invention, at 1 kHz and 20° C., is preferably 1 or more, more preferably 2 or more and very preferably 3 or more.

The Δn of the liquid-crystal media according to the present invention, at 589 nm (Na$^D$) and 20° C., is preferably in the range from 0.200 or more to 0.90 or less, more preferably in the range from 0.250 or more to 0.90 or less, even more preferably in the range from 0.300 or more to 0.85 or less and very particularly preferably in the range from 0.350 or more to 0.800 or less.

In a preferred embodiment of the present application, the Δn of the liquid-crystal media in accordance with the present invention is preferably 0.50 or more, more preferably 0.55 or more.

The compounds of the formulae I to III in each case include dielectrically positive compounds having a dielectric anisotropy of greater than 3, dielectrically neutral compounds having a dielectric anisotropy of less than 3 and greater than −1.5 and dielectrically negative compounds having a dielectric anisotropy of −1.5 or less.

The compounds of the formulae I, II and III are preferably dielectrically positive.

In the present application, the expression dielectrically positive describes compounds or components where Δε>3.0, dielectrically neutral describes those where −1.5≤Δε≤3.0 and dielectrically negative describes those where Δε<−1.5. Δε is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

Δε is defined as $(\varepsilon_{\parallel} - \varepsilon_{\perp})$, while $\varepsilon_{ave.}$ is $(\varepsilon_{\parallel} + 2\varepsilon_{\perp})/3$.

The host mixture used for dielectrically positive compounds is mixture ZLI-4792 and that used for dielectrically neutral and dielectrically negative compounds is mixture ZLI-3086, both from Merck KGaA, Germany. The absolute values of the dielectric constants of the compounds are determined from the change in the respective values of the host mixture on addition of the compounds of interest. The values are extrapolated to a concentration of the compounds of interest of 100%.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy (Δn) is determined at a wavelength of 589.3 nm. The dielectric anisotropy (Δε) is determined at a frequency of 1 kHz. The threshold voltages, as well as all other electro-optical properties, are determined using test cells produced at Merck KGaA, Germany. The test cells for the determination of Δε have a cell thickness of approximately 20 μm. The electrode is a circular ITO electrode having an area of 1.13 cm$^2$ and a guard ring. The orientation layers are SE-1211 from Nissan Chemicals, Japan, for homeotropic orientation ($\varepsilon_{\parallel}$) and polyimide AL-1054 from Japan Synthetic Rubber, Japan, for homogeneous orientation ($\varepsilon_{\perp}$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The characteristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency range as described in A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, pp. 545-548.

In this respect, see also: A. Gaebler, F. Gölden, S. Müller, A. Penirschke and R. Jakoby "Direct Simulation of Material Permittivites . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) capillary. The capillary has an internal radius of 180 μm and an external radius of 350 μm. The effective length is 2.0 cm. The filled capillary is introduced into the centre of the cavity with a resonance frequency of 30 GHz. This cavity has a length of 6.6 mm, a width of 7.1 mm and a height of 3.6 mm. The input signal (source) is then applied, and the result of the output signal is recorded using a commercial vector network analyser.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in A. Penirschke, S. Müller, P. Scheele, C. Weil, M. Wittek, C. Hock and R. Jakoby: "Cavity Perturbation Method for Characterization of Liquid Crystals up to 35 GHz", 34$^{th}$ European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla. The alignment of the magnets is set correspondingly and then rotated correspondingly through 90°.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

The liquid-crystal media according to the invention preferably have nematic phases in preferred ranges given above. The expression have a nematic phase here means on the one hand that no smectic phase and no crystallisation are observed at low temperatures at the corresponding temperature and on the other hand that no clearing occurs on heating from the nematic phase. The investigation at low temperatures is carried out in a flow viscometer at the corresponding temperature and checked by storage in test cells having a layer thickness of 5 µm for at least 100 hours. At high temperatures, the clearing point is measured in capillaries by conventional methods.

Furthermore, the liquid-crystal media according to the invention are characterised by high optical anisotropy values in the visible range, especially at a wavelength of 589.0 nm (i.e. at the Na"D" line). The birefringence at 589 nm is preferably 0.20 or more, particularly preferably 0.25 or more, particularly preferably 0.30 or more, particularly preferably 0.40 or more and very particularly preferably 0.45 or more. In addition, the birefringence is preferably 0.80 or less.

The liquid crystals employed preferably have a positive dielectric anisotropy. This is preferably 2 or more, preferably 4 or more, particularly preferably 6 or more and very particularly preferably 10 or more.

Furthermore, the liquid-crystal media according to the invention are characterised by high anisotropy values in the microwave range. The birefringence at about 8.3 GHz is, for example, preferably 0.14 or more, particularly preferably 0.15 or more, particularly preferably 0.20 or more, particularly preferably 0.25 or more and very particularly preferably 0.30 or more. In addition, the birefringence is preferably 0.80 or less.

The dielectric anisotropy in the microwave range is defined as $$\Delta\varepsilon_r \equiv (\varepsilon_{r,\parallel} - \varepsilon_{r,\perp}).$$

The tunability (τ) is defined as $$\tau \equiv (\Delta\varepsilon_r / \varepsilon_{r,\parallel}).$$

The material quality (η) is defined as $$\eta \equiv (\tau / \tan \delta\varepsilon_{r,max}), \text{ where}$$

the maximum dielectric loss is $$\tan \delta_{\varepsilon_r,max} \equiv \max\{\tan \delta_{\varepsilon_r,\perp}; \tan \delta_{\varepsilon_r,\parallel}\}.$$

The material quality (η) of the preferred liquid-crystal materials is 6 or more, preferably 8 or more, preferably 10 or more, preferably 15 or more, preferably 17 or more, preferably 20 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, liquid crystals having a negative value of the dielectric anisotropy can also advantageously be used.

The liquid crystals employed are either individual substances or mixtures. They preferably have a nematic phase.

The term "alkyl" preferably encompasses straight-chain and branched alkyl groups having 1 to 15 carbon atoms, in particular the straight-chain groups methyl, ethyl, propyl, butyl, pentyl, hexyl and heptyl. Groups having 2 to 10 carbon atoms are generally preferred.

The term "alkenyl" preferably encompasses straight-chain and branched alkenyl groups having 2 to 15 carbon atoms, in particular the straight-chain groups. Particularly preferred alkenyl groups are $C_2$- to $C_7$-1E-alkenyl, $C_4$- to $C_7$-3E-alkenyl, $C_5$- to $C_7$-4-alkenyl, $C_6$- to $C_7$-5-alkenyl and $C_7$-6-alkenyl, in particular $C_2$- to $C_7$-1E-alkenyl, $C_4$- to $C_7$-3E-alkenyl and $C_5$- to $C_7$-4-alkenyl. Examples of further preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4 Z-hexenyl, 4E-hexenyl, 4 Z-heptenyl, 5-hexenyl, 6-heptenyl and the like. Groups having up to 5 carbon atoms are generally preferred.

The term "fluoroalkyl" preferably encompasses straight-chain groups having a terminal fluorine, i.e. fluoromethyl, 2-fluoroethyl, 3-fluoropropyl, 4-fluoro-butyl, 5-fluoropentyl, 6-fluorohexyl and 7-fluoroheptyl. However, other positions of the fluorine are not excluded.

The term "oxaalkyl" or "alkoxyalkyl" preferably encompasses straight-chain radicals of the formula $C_nH_{2n+1}$—O—$(CH_2)_m$, in which n and m each, independently of one another, denote 1 to 10. Preferably, n is 1 and m is 1 to 6.

Compounds containing a vinyl end group and compounds containing a methyl end group have low rotational viscosity.

In the present application, both high-frequency technology and hyper-frequency technology denote applications having frequencies in the range from 1 MHz to 1 THz, preferably from 1 GHz to 500 GHz, more preferably 2 GHz to 300 GHz, particularly preferably from about 5 GHz to 150 GHz.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

Preferably the media according to the present invention comprise one or more chiral compounds as chiral dopants in order to adjust their cholesteric pitch. Their total concentration in the media according to the instant invention is preferably in the range 0.05% to 15%, more preferably from 1% to 10% and most preferably from 2% to 6%.

Optionally the media according to the present invention may comprise further liquid crystal compounds in order to adjust the physical properties. Such compounds are known to the expert. Their concentration in the media according to the instant invention is preferably 0% to 30%, more preferably 0.1% to 20% and most preferably 1% to 15%.

The response times are given as rise time ($\tau_{on}$) for the time for the change of the relative tuning, respectively of the relative contrast for the electro-optical response, from 0% to 90% ($t_{90}$-$t_0$), i.e. including the delay time ($t_{10}$-$t_0$), as decay time ($\tau_{off}$) for the time for the change of the relative tuning, respectively of the relative contrast for the electro-optical response, from 100% back to 10% ($t_{100}$-$t_{10}$) and as the total response time ($\tau_{total}=\tau_{on}+\tau_{off}$), respectively.

The liquid-crystal media according to the invention consist of a plurality of compounds, preferably 3 to 30, more preferably 4 to 20 and very preferably 4 to 16 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multibottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_lH_{2l+1}$ or $C_nH_{2n-1}$, $C_mH_{2m-1}$ and $C_lH_{2l-1}$ denote straight-chain alkyl or alkenyl, preferably 1-E-alkenyl, respectively, in each case having n, m or l C atoms. Table A lists the codes used for the ring elements of the core structures of the compounds, while Table B shows the linking groups. Table C gives the meanings of the codes for the left-hand or right-hand end groups. Table D shows illustrative structures of compounds with their respective abbreviations.

TABLE A

Ring elements

C, D, DI, A, AI, P, G, GI, U, UI, Y, M, MI, N, NI, Np

TABLE A-continued
| Ring elements | | |
|---|---|---|
| N3f | 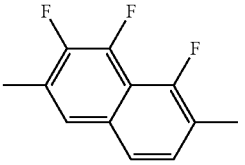 | |
| N3fI | 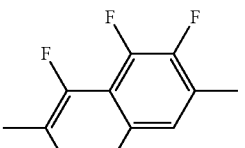 | |
| tH | 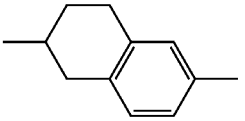 | |
| tHI | 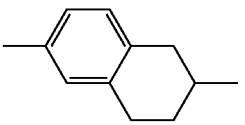 | |
| tH2f | 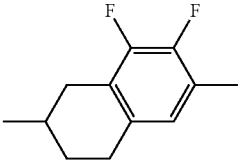 | |
| tH2fI | 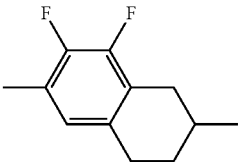 | |
| dH | 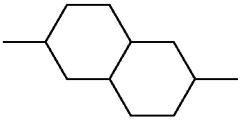 | |
| K | 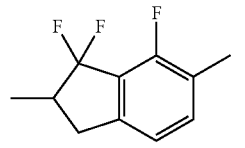 | |
| KI | 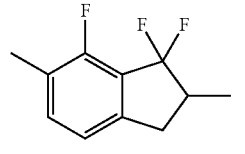 | |
| L | 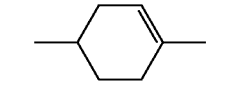 | |
| LI | | |
| F | | |
| FI | | |
| P(o) | $C_oH_{2o+1}$ | |
| PI(o) | $C_oH_{2o+1}$ | |
| P(i3) | | |
| PI(ic3) | | |
| P(t4) | | |
| PI(t4) | | |
| P(c3) | | |

TABLE A-continued
| Ring elements | |
|---|---|
| PI(c3) | 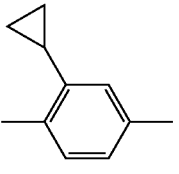 |
| P(c4) | 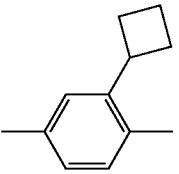 |
| PI(c4) | 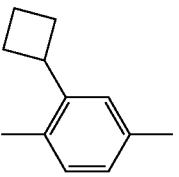 |
| P(c5) | 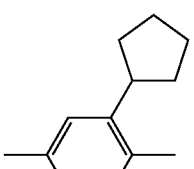 |
| PI(c5) | 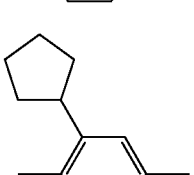 |
| P(e5) | 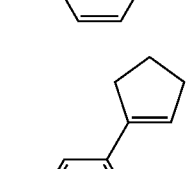 |
| PI(e5) | 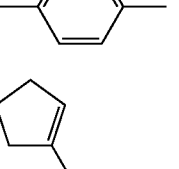 |
| P(c6) | 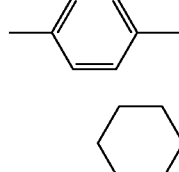 |
| PI(c6) | 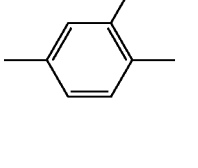 |
| P(e6) | 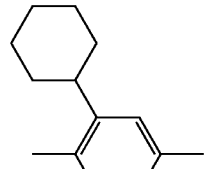 |
| PI(e6) | 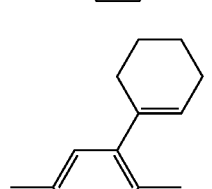 |
| GI(o) | 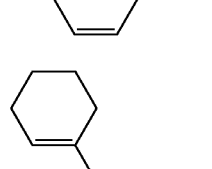 |
| | $o \in \{1;2;3;4;5;6\}$ |
| G(o) | 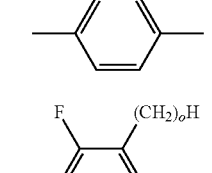 |
| | $o \in \{1;2;3;4;5;6\}$ |
| GI(i3) | 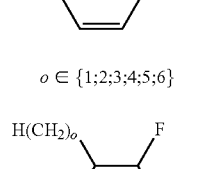 |
| G(i3) | 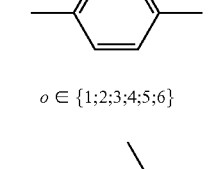 |
| GI(t4) | 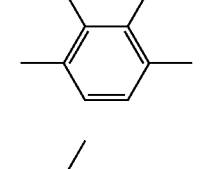 |

TABLE A-continued

Ring elements

G(t4)

GI(c3)

G(c3)

GI(c4)

G(c4)

GI(c5)

G(c5)

GI(e5)

G(e5)

GI(c6)

G(c6)

GI(e6)

G(e6)

N(1,4)

TABLE B

| | Linking groups | | |
|---|---|---|---|
| E | —CH$_2$CH$_2$— | Z | —CO—O— |
| V | —CH=CH— | ZI | —O—CO— |
| X | —CF=CH— | O | —CH$_2$—O— |
| XI | —CH=CF— | OI | —O—CH$_2$— |
| B | —CF=CF— | Q | —CF$_2$—O— |
| T | —C≡C— | QI | —O—CF$_2$— |
| W | —CF$_2$CF$_2$— | | |

TABLE C

| End groups | | | |
|---|---|---|---|
| Left-hand side | | Right-hand side | |
| Used alone | | | |
| -n- | $C_nH_{2n+1}$— | -n | —$C_nH_{2n+1}$ |
| -nO- | $C_nH_{2n+1}$—O— | -On | —O—$C_nH_{2n+1}$ |
| -V- | $CH_2$=CH— | -V | —CH=$CH_2$ |
| -nV- | $C_nH_{2n+1}$—CH=CH— | -nV | —$C_nH_{2n}$—CH=$CH_2$ |
| -Vn- | $CH_2$=CH—$C_nH_{2n+1}$— | -Vn | —CH=CH—$C_nH_{2n+1}$ |
| -nVm- | $C_nH_{2n+1}$—CH=CH—$C_mH_{2m}$— | -nVm | —$C_nH_{2n}$—CH=CH—$C_mH_{2m+1}$ |
| -N- | N≡C— | -N | —C≡N |
| -S- | S=C=N— | -S | —N=C=S |
| -F- | F— | -F | —F |
| -CL- | Cl— | -CL | —Cl |
| -M- | $CFH_2$— | -M | —$CFH_2$ |
| -D- | $CF_2H$— | -D | —$CF_2H$ |
| -T- | $CF_3$— | -T | —$CF_3$ |
| -MO- | $CFH_2O$— | -OM | —$OCFH_2$ |
| -DO- | $CF_2HO$— | -OD | —$OCF_2H$ |
| -TO- | $CF_3O$— | -OT | —$OCF_3$ |
| -FXO- | $CF_2$=CH—O— | -OXF | —O—CH=$CF_2$ |
| -A- | H—C≡C— | -A | —C≡C—H |
| -nA- | $C_nH_{2n+1}$—C≡C— | -An | —C≡C—$C_nH_{2n+1}$ |
| -NA- | N≡C—C≡C— | -AN | —C≡C—C≡N |
| Used in combination with others | | | |
| -...A...- | —C≡C— | -...A... | —C≡C— |
| -...V...- | —CH=CH— | -...V... | —CH=CH— |
| -...Z...- | —CO—O— | -...Z... | —CO—O— |
| -...ZI...- | —O—CO— | -...ZI... | —O—CO— |
| -...K...- | —CO— | -...K... | —CO— |
| -...W...- | —CF=CF— | -...W... | —CF=CF— | in which n and m each denote integers, and the three dots " . . . " are place-holders for other abbreviations from this table.

The following table shows illustrative structures together with their respective abbreviations. These are shown in order to illustrate the meaning of the rules for the abbreviations. They furthermore represent compounds which are preferably used.

TABLE D

Illustrative structures

The following illustrative structures are compounds, which are particularly preferably employed, having a terminal —NSC group:

$C_nH_{2n+1}$—[phenyl]—[phenyl with F]—NCS    PG-n-S $C_nH_{2n+1}$—[phenyl]—[phenyl with F, F]—NCS    PU-n-S $C_nH_{2n+1}$—[phenyl]—[phenyl]—[phenyl with F]—NCS    PPG-n-S TABLE D-continued
Illustrative structures
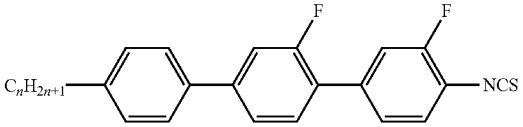  PGG-n-S
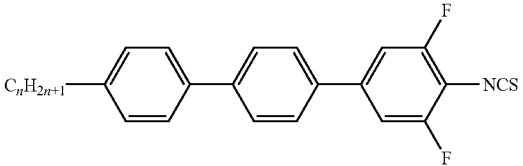  PPU-n-S
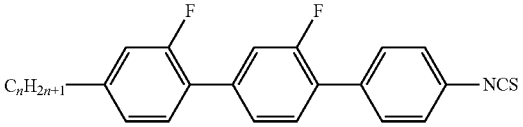  GGP-n-S
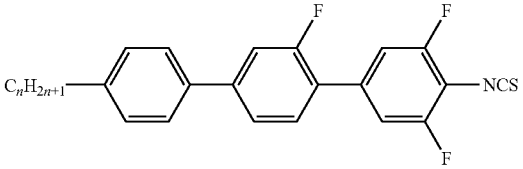  PGU-n-s
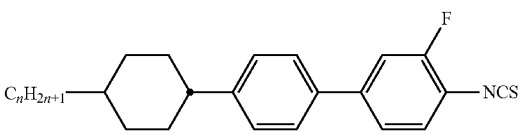  CPG-n-S
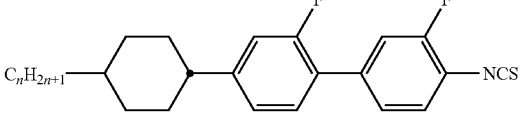  CGG-n-S
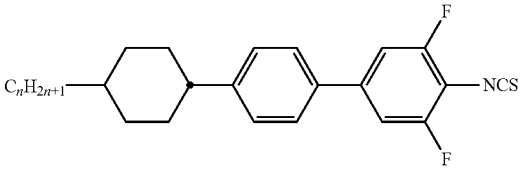  CPU-n-S
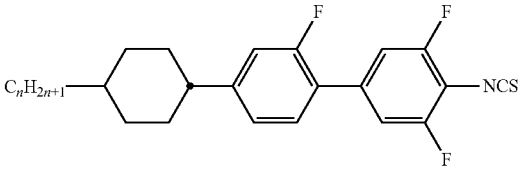  CGU-n-S
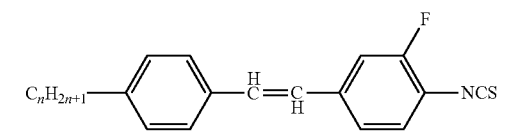  PVG-n-S
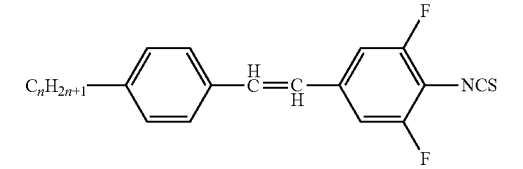  PVU-n-S TABLE D-continued
Illustrative structures
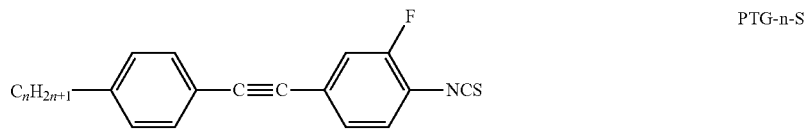
PTG-n-S
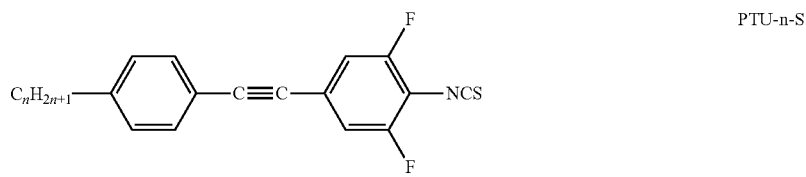
PTU-n-S
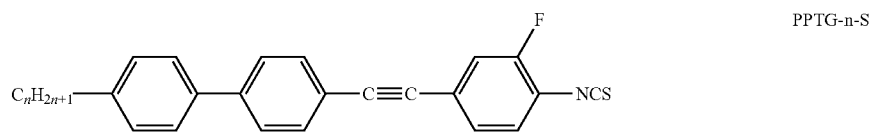
PPTG-n-S
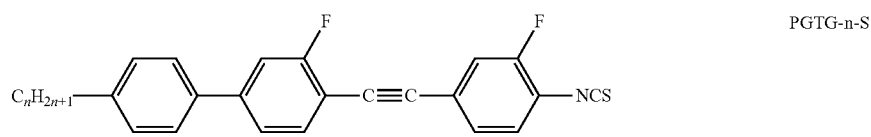
PGTG-n-S
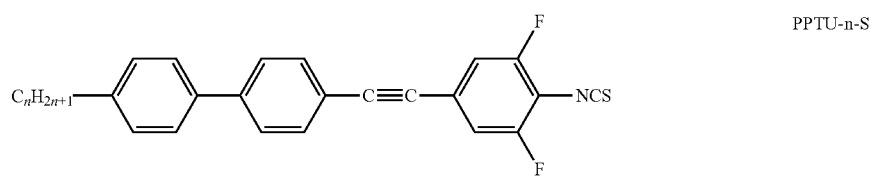
PPTU-n-S
The following illustrative structures are compounds, which are preferably additionally used in the media:
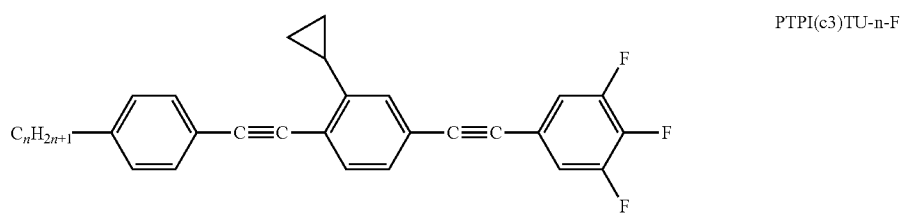
PTPI(c3)TU-n-F
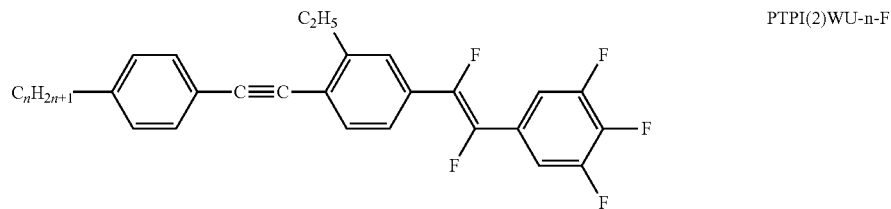
PTPI(2)WU-n-F
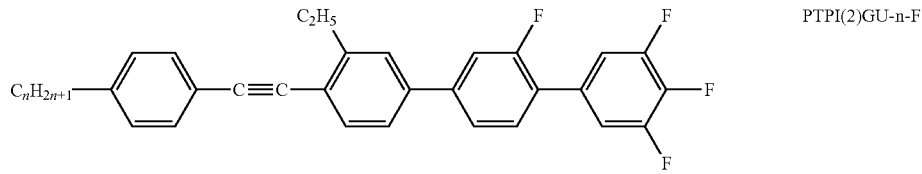
PTPI(2)GU-n-F TABLE D-continued
Illustrative structures
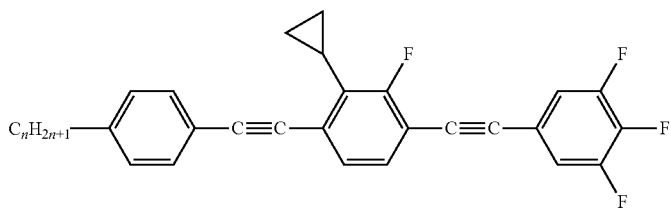
PTG(c3)TU-n-F
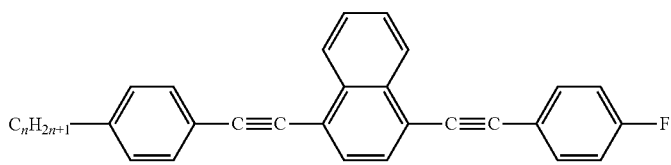
PTN(1,4)TP-n-F
The following illustrative structures are auxiliary compounds, which are optionally employed, having three 6-membered rings:
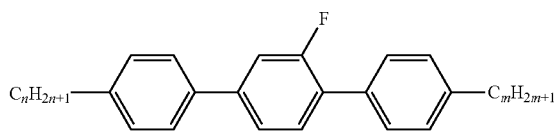
PGP-n-m
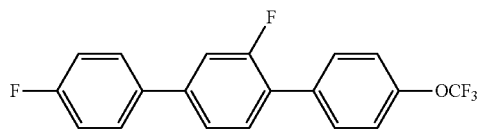 [SMILES: Fc1ccc(-c2ccc(-c3ccc(OC(F)(F)F)cc3)c(F)c2)cc1]
PGP-F-OT
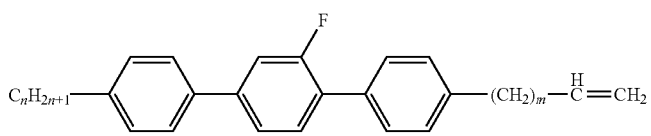
PGP-n-mV
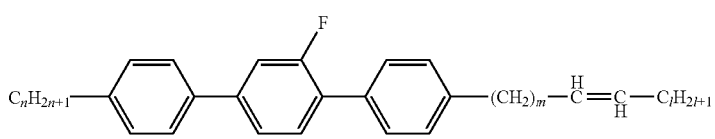
PGP-n-mVI
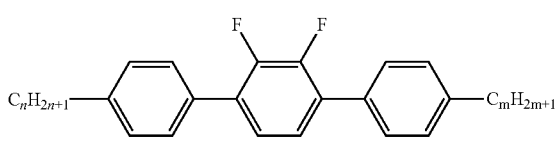
PYP-n-m
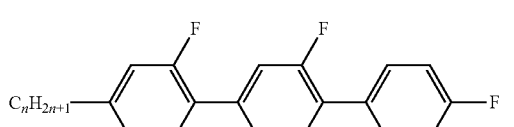
GGP-n-F
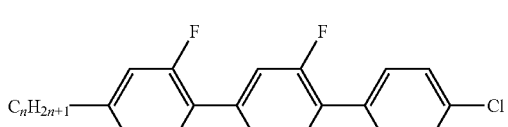
GGP-n-CL
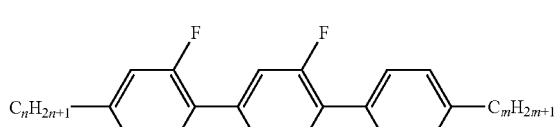
GGP-n-m TABLE D-continued Illustrative structures

| Structure | Code |
|---|---|
| (structure) | PGIGI-n-F |
| (structure) | PGIGI-n-CL |
| (structure) | PGU-n-F |
| (structure) | PGU-n-CL |
| (structure) | PGU-n-OT |
| (structure) | PPTUI-n-m |
| (structure) | PPTY-n-m |

The following illustrative structures are auxiliary compounds, which are optionally employed, having four 6-membered rings:

| Structure | Code |
|---|---|
| (structure) | PGGP-n-m |
| (structure) | PGIGP-n-m |

TABLE D-continued

| Illustrative structures | |
|---|---|
| [structure] | PGIGP-n-Om |
| [structure] | PGIGP-nO-M |
| [structure] | PYGP-n-m |
| [structure] | GGPP-n-m |
| [structure] | PPGU-n-F |
| [structure] | PPGU-Vn-F |

Illustrative structures of dielectrically neutral compounds which may additionally be employed:

| | |
|---|---|
| [structure] | CPTP-n-m |
| [structure] | CPPC-n-m |
| [structure] | CGPC-n-m |
| [structure] | CCZPC-n-m |
| [structure] | CPGP-n-m |

TABLE D-continued

Illustrative structures $C_nH_{2n+1}$—⬡—⌬—⌬(F)—⌬—$(CH_2)_m$—CH=CH$_2$  CPGP-n-mV $C_nH_{2n+1}$—⬡—⌬—⌬(F)—⌬—$(CH_2)_m$—CH=CH—$C_lH_{2l+1}$  CPGP-n-mVI Illustrative structures of further compounds which may additionally be employed:

$C_nH_{2n+1}$—⬡—⌬(2-F)—⌬(3,4,5-F)  CGU-n-F $C_nH_{2n+1}$—⬡—⬡—⌬—⌬(3,4,5-F)  CCPU-n-F $C_nH_{2n+1}$—⬡—⬡—⌬(2-F)—⌬(3,4,5-F)  CCGU-n-F $C_nH_{2n+1}$—⬡—⌬—⌬(2-F)—⌬(3,4,5-F)  CPGU-n-F $C_nH_{2n+1}$—⬡—⌬—⌬(2-F)—⌬(3,5-F)—OCF$_3$  CPGU-n-OT $C_nH_{2n+1}$—⌬—⌬(3,5-F)—CF$_2$—O—⌬(2,3,5-F)  PUQU-n-F

TABLE D-continued

| Illustrative structures | |
|---|---|
| [structure] | PGUQU-n-F |
| [structure] | DPGU-n-F |
| [structure] | DPGU-n-OT |
| [structure] | APGP-n-m |

The following table, Table E, shows illustrative compounds which can be used as stabiliser in the mesogenic media in accordance with the present invention. The total concentration of these and similar compounds in the media is preferably 5% or less.

TABLE E

[structures of stabiliser compounds]

TABLE E-continued
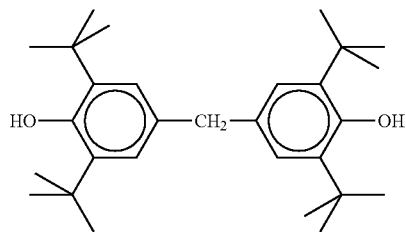
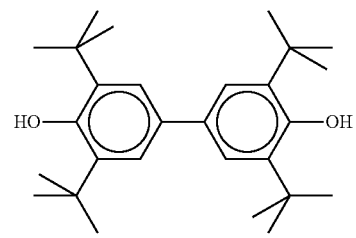
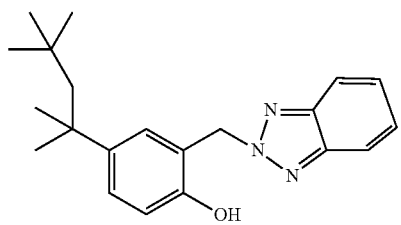 [SMILES: CC(C)(C)CC(C)(C)c1ccc(O)c(Cn2nc3ccccc3n2)c1]
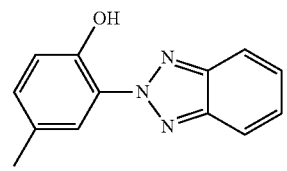 [SMILES: Cc1ccc(O)c(-n2nc3ccccc3n2)c1]
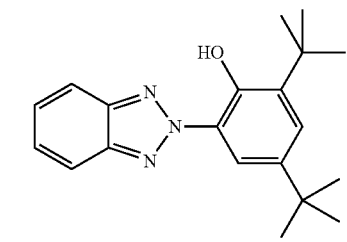 [SMILES: CC(C)(C)c1cc(-n2nc3ccccc3n2)c(O)c(C(C)(C)C)c1]
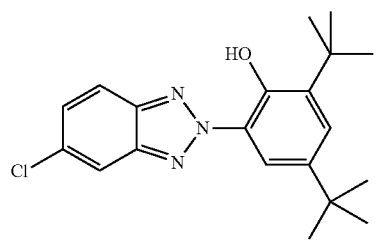 [SMILES: CC(C)(C)c1cc(-n2nc3ccc(Cl)cc3n2)c(O)c(C(C)(C)C)c1]
TABLE E-continued
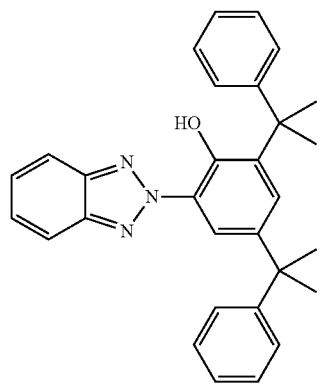 [SMILES: CC(C)(c1ccccc1)c1cc(-n2nc3ccccc3n2)c(O)c(C(C)(C)c2ccccc2)c1]
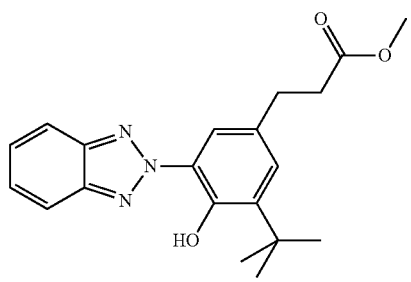 [SMILES: COC(=O)CCc1cc(-n2nc3ccccc3n2)c(O)c(C(C)(C)C)c1]
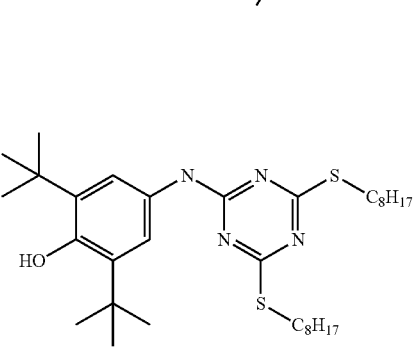
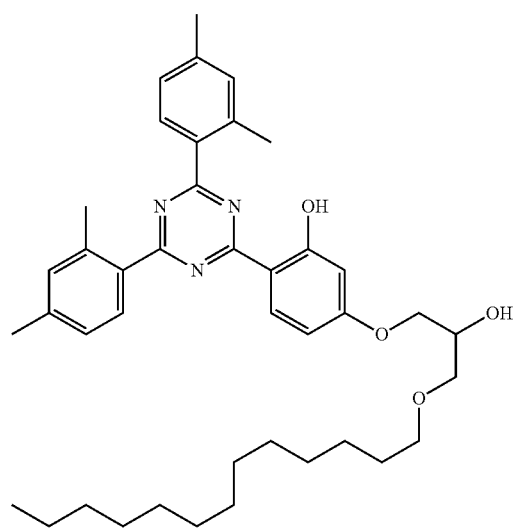 [SMILES: CCCCCCCCCCCCCOCC(O)COc1ccc(-c2nc(-c3ccc(C)cc3C)nc(-c3ccc(C)cc3C)n2)c(O)c1]

TABLE E-continued
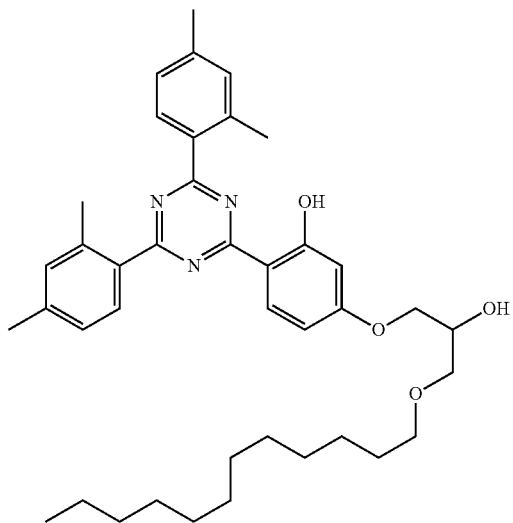 [SMILES: CCCCCCCCCCCCOCC(O)COc1ccc(-c2nc(-c3ccc(C)cc3C)nc(-c3ccc(C)cc3C)n2)c(O)c1]
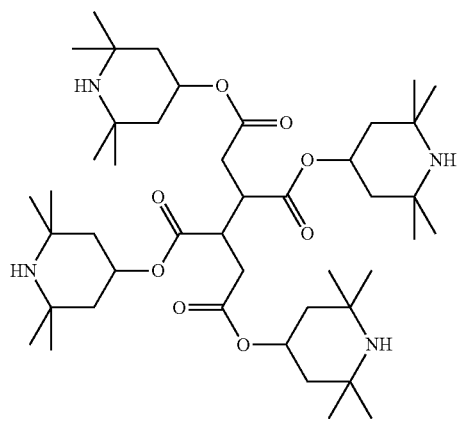 [SMILES: CC1(C)CC(OC(=O)CC(C(=O)OC2CC(C)(C)NC(C)(C)C2)C(CC(=O)OC2CC(C)(C)NC(C)(C)C2)C(=O)OC2CC(C)(C)NC(C)(C)C2)CC(C)(C)N1]
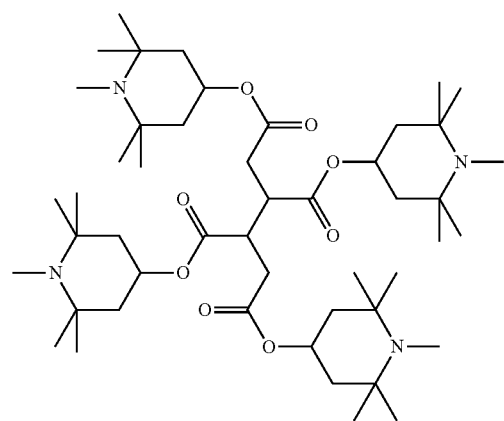
TABLE E-continued
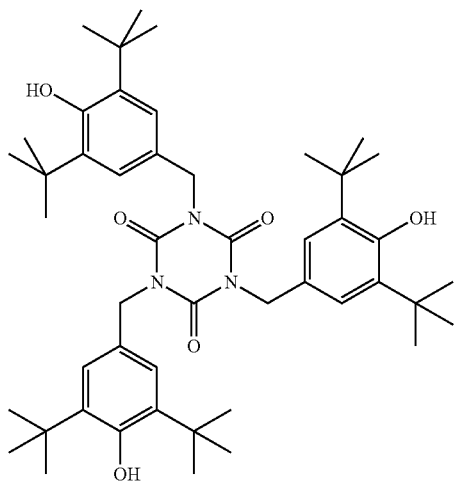 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]
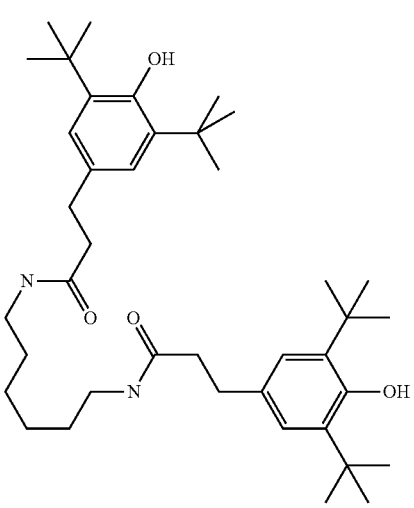 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
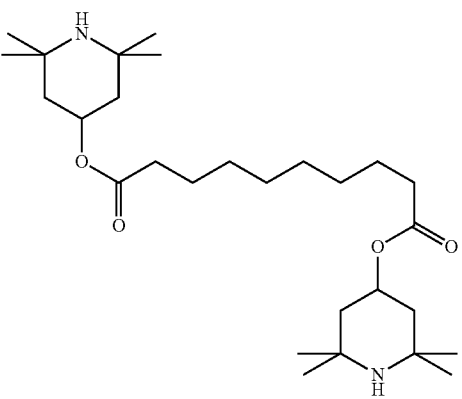

TABLE E-continued

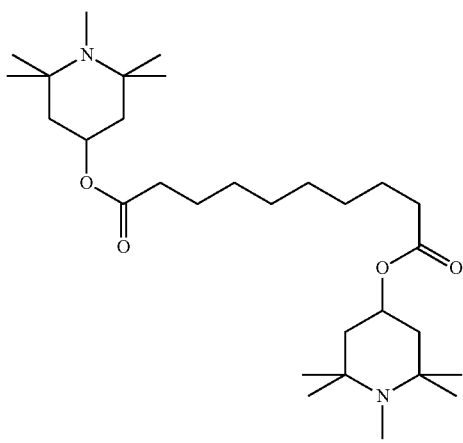

TABLE E-continued

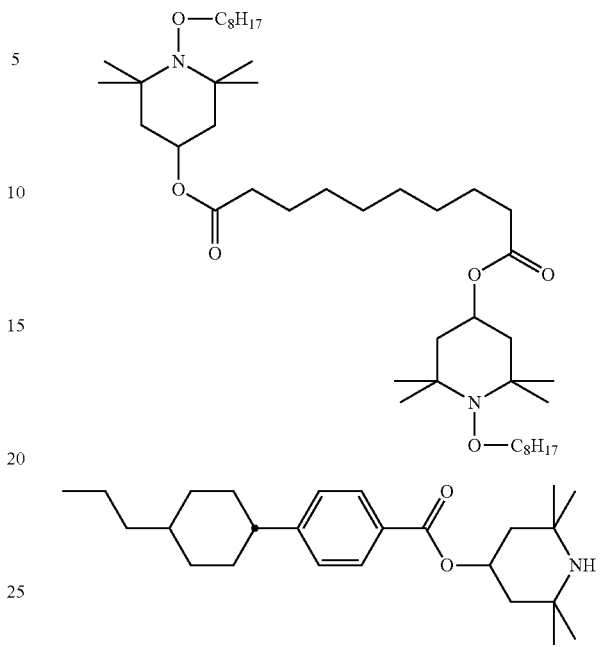

In a preferred embodiment of the present invention, the mesogenic media comprise one or more compounds selected from the group of the compounds from Table E.

The following table, Table F, shows illustrative compounds which can preferably be used as chiral dopants in the mesogenic media in accordance with the present invention.

TABLE F

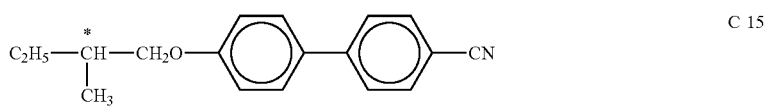

C 15

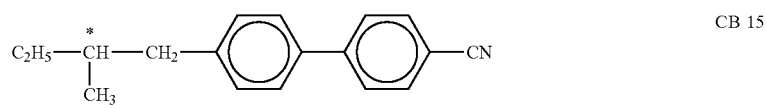

CB 15

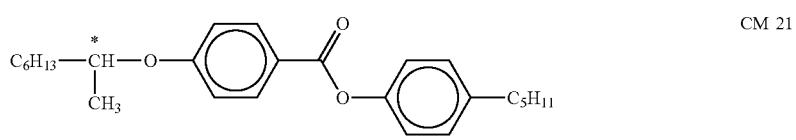

CM 21

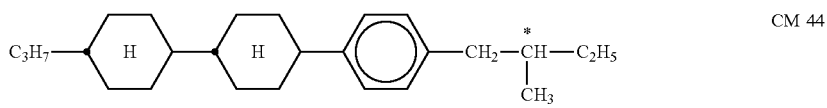

CM 44

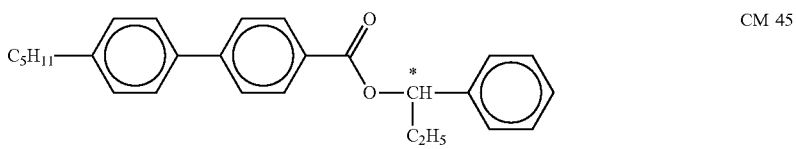

CM 45

TABLE F-continued
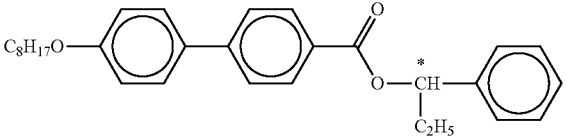 CM 47
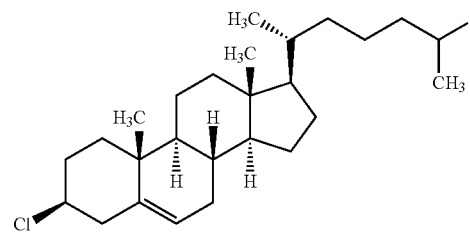 CC
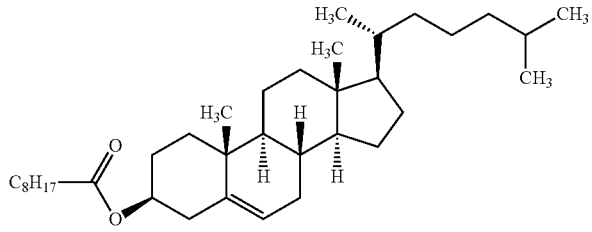 CN
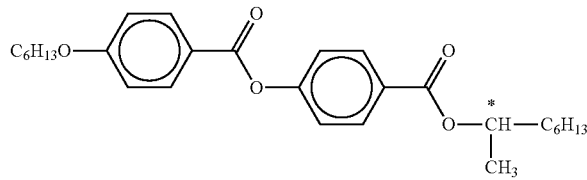 R/S-811
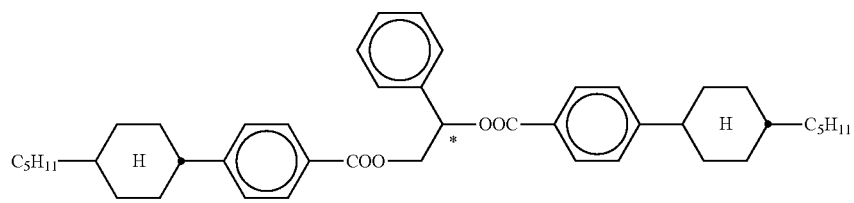 R/S-1011
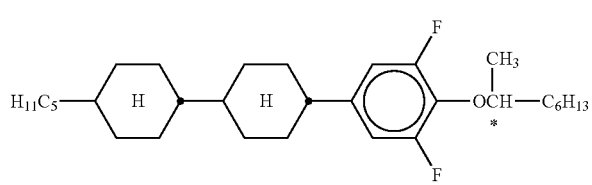 R/S-2011
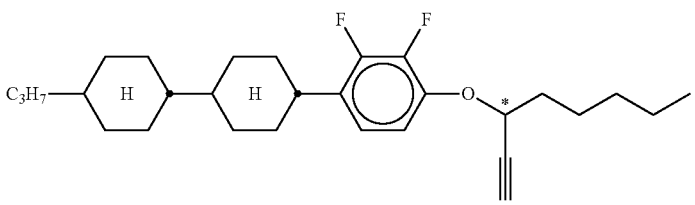 R/S-3011
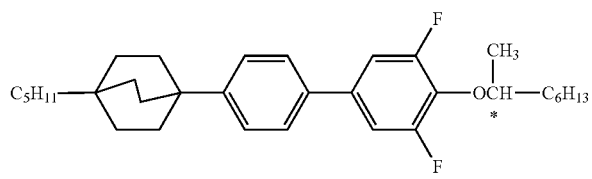 R/S-4011

TABLE F-continued

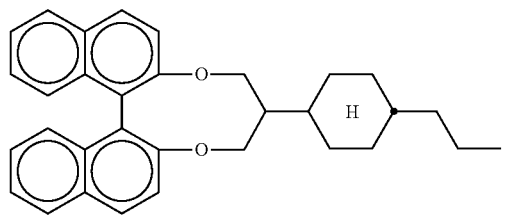

R/S-5011

In a preferred embodiment of the present invention, the mesogenic media comprise one or more compounds selected from the group of the compounds from Table F.

The mesogenic media in accordance with the present application preferably comprise two or more, preferably four or more, compounds selected from the group consisting of the compounds from the above tables.

The liquid-crystal media in accordance with the present invention preferably comprise
seven or more, preferably eight or more, compounds, preferably compounds having three or more, preferably four or more, different formulae, selected from the group of the compounds from Table D.

EXAMPLES

The following examples illustrate the present invention without limiting it in any way.

However, it is clear to the person skilled in the art from the physical properties what properties can be achieved and in what ranges they can be modified. In particular, the combination of the various properties which can preferably be achieved is thus well defined for the person skilled in the art.

Synthesis Example 1

Step 1: 2,6-Difluoro-4-[2-fluoro-4-[4-(4-propylphenyl)phenyl]phenyl]aniline

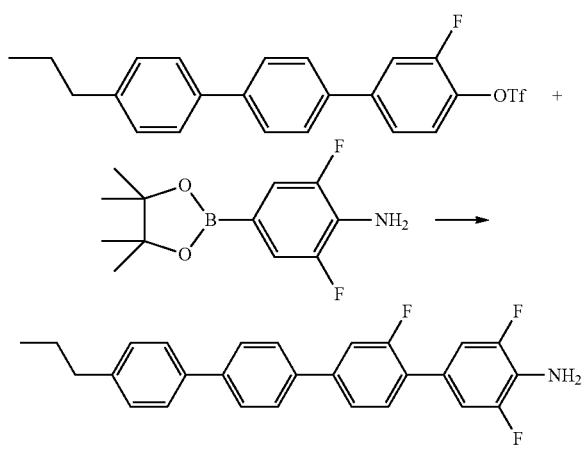

11.8 g (26.7 mmol) [2-fluoro-4-[4-(4-propylphenyl)phenyl]phenyl]trifluoromethane sulfonate and 10.4 g (40.1 mmol) 2,6-difluoro-4-(4,4,5,5-tetramethyl-1,3,2-dioxaborolan-2-yl)aniline are dissolved in 30 ml tetrahydrofuran. Then, 15 ml water, 40 µl hydrazinium hydrate, 375 mg bis(triphenylphosphine palladium(II)choride and sodium metaborate octahydrate are added and the reaction is heated under reflux for 3 h. The reaction is filtered, evaporated and the crude product is purified by chromatography and recrystallised from toluene. 2,6-Difluoro-4-[2-fluoro-4-[4-(4-propylphenyl)phenyl]phenyl]aniline is obtained as colourless crystals.

Step 2: 1,3-Difluoro-5-[2-fluoro-4-[4-(4-propylphenyl)phenyl]phenyl]-2-isothiocyanato-benzene

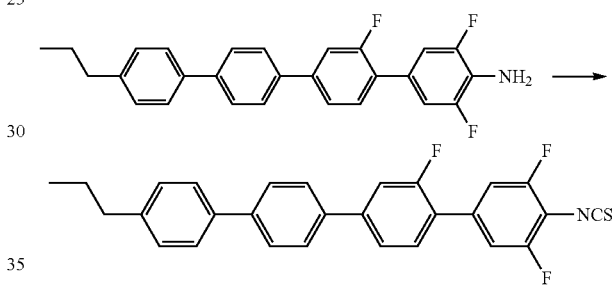

8.9 (20.9 mmol) 2,6-difluoro-4-[2-fluoro-4-[4-(4-propylphenyl)-phenyl]phenyl]aniline and 5.97 g (33 mmol) thiocarbonyl diimidazole are dissolved in 100 ml dichloromethane and heated under reflux for 3 d. The reaction is filtered, the filtrate evaporated and the crude product is purified by chromatography to give 1,3-difluoro-5-[2-fluoro-4-[4-(4-propyl-phenyl)phenyl]phenyl]-2-isothiocyanato-benzene as colourless crystals.

Phase Sequence: K 127 SmC 132 N 354 I.
$\Delta n = 0.4604$[1]
$\Delta \varepsilon = 23.5$[1]

[1] Extrapolated from a 10% solution in ZLI-4292

Comparative Example 1 (Example 4 from EP2982730)

A liquid-crystal mixture C-1 having the composition and properties as indicated in the following table is prepared and characterized with respect to its general physical properties and its applicability in microwave applications.

| | Composition | | | |
|---|---|---|---|---|
| | Compound | | | |
| No | Abbreviation | Conc./mass-% | Physical Properties | |
| 1 | GGP-3-S | 8.0 | T(N, I)/° C.= | 98 |
| 2 | PGG-3-S | 12.0 | $\varepsilon_{\parallel}$ (20° C., 1 kHz)= | 26.7 |

-continued

| | Composition | | | |
|---|---|---|---|---|
| | Compound | | | |
| No | Abbreviation | Conc./mass-% | Physical Properties | |
| 3 | PGU-3-S | 12.0 | $\Delta\varepsilon$ (20° C., 1 kHz)= | 5.1 |
| 4 | PVG-3-S | 6.0 | $k_{11}$ (20° C.)/pN | 17.7 |
| 5 | PVG-4-S | 18.0 | $k_{33}$ (20° C.)/pN | 15.7 |
| 6 | PTG-3-S | 10.0 | $V_0$ (20° C.)/V | 0.96 |
| 7 | PTG-5-S | 18.0 | $\gamma_1$ (20° C.)/mPa · s= | 698 |
| 8 | PTU-3-S | 10.0 | $\tan\delta_{\varepsilon r, max}$ (20° C., 19 GHz)= | 0.0189 |
| 9 | PPTU-4-S | 6.0 | $\tau$ (20° C., 19 GHz)= | 0.336 |
| $\Sigma$ | | 100.0 | $\eta$ (20° C., 19 GHz)= | 17.9 |

This mixture comprises 68% of stilbene and tolane derivatives and 32% of compounds of formula I.

Comparative Example 2 (Example 14 from EP2982730)

A liquid-crystal mixture C-2 having the composition and properties as indicated in the following table is prepared and characterized with respect to its general physical properties and its applicability in microwave

| | Composition | | | |
|---|---|---|---|---|
| | Compound | | | |
| No | Abbreviation | Conc./mass-% | Physical Properties | |
| 1 | PU-3-S | 8.0 | T(N, I)/° C.= | 124 |
| 2 | PVG-4-S | 8.0 | $\varepsilon_{\parallel}$(20° C., 1 kHz)= | 26.2 |
| 3 | PVG-5-S | 8.0 | $\Delta\varepsilon$(20° C., 1 kHz)= | 4.6 |
| 4 | PTU-3-S | 8.0 | $\gamma_1$ (20° C.)/mPa · s= | 311 |
| 5 | PTU-5-S | 8.0 | $k_1$ (20° C.)/pN= | 16.2 |
| 6 | CGU-4-S | 15.0 | $k_3/k_1$ (20° C.)= | 1.28 |
| 7 | CGU-5-S | 15.0 | $V_0$ (20° C.)/V= | 0.91 |
| 8 | PGU-3-S | 16.0 | | |
| 9 | PPTU-4-S | 7.0 | $\varepsilon_{r,\perp}$ (20° C., 19 GHz)= | 2.37 |
| 10 | PPTU-5-S | 7.0 | $\varepsilon_{r,\parallel}$ (20° C., 19 GHz)= | 3.48 |
| $\Sigma$ | | 100.0 | $\tan\delta_{\varepsilon r,\perp}$ (20° C., 19 GHz)= | 0.0120 |
| | | | $\tan\delta_{\varepsilon r,\parallel}$ (20° C., 19 GHz)= | 0.0066 |
| | | | $\tau$ (20° C., 19 GHz)= | 0.318 |
| | | | $\eta$ (20° C., 19 GHz)= | 26.5 |

This mixture comprises 46% of stilbene and tolane derivatives and 54% of compounds of formula I.

Mixture Examples

Liquid-crystal mixtures M-1 to M-5 having the composition and properties as indicated in the following tables are prepared and characterized with respect to their general physical properties and their applicability in microwave components at 19 GHz.

Mixture Example M-1

| | Composition | | | |
|---|---|---|---|---|
| | Compound | | | |
| No | Abbreviation | Conc./[mass-%] | Physical Properties | |
| 1 | PU-3-S | 20.0 | T(N, I) [° C.]= | 134 |
| 2 | PGU-3-S | 15.0 | $\varepsilon_{\parallel}$(20° C., 1 kHz)= | 27.3 |
| 3 | PGU-4-S | 15.0 | $\Delta\varepsilon$(20° C., 1 kHz)= | 22.6 |
| 4 | CPU-2-S | 15.0 | $\gamma_1$ (20° C.)/mPa · s= | 324 |
| 5 | CPU-3-S | 10.0 | $k_1$= | 14.2 |
| 6 | CPU-4-S | 15.0 | $k_3$= | 21.8 |
| 7 | CPU-5-S | 10.0 | $V_0$ [V]= | 0.84 |
| $\Sigma$ | | 100.0 | | |
| | | | $\tan\delta_{\varepsilon r,\perp}$ (20° C., 19 GHz)= | 0.0128 |
| | | | $\tan\delta_{\varepsilon r,\parallel}$ (20° C., 19 GHz)= | 0.0069 |
| $\varepsilon$ | | | $\tau$ (20° C., 19 GHz)= | 0.291 |
| $\varepsilon$ | | | $\varepsilon_{r,\parallel}$ (20° C., 19 GHz)= | 3.3697 |
| | | | $\varepsilon_{r,\perp}$ (20° C., 19 GHz)= | 2.3886 |
| | | | $\eta$ (20° C., 19 GHz)= | 22.7 |

The mixture M-1 comprises 100% of compounds of formula I. This mixture is very well suitable for applications in the microwave range, in particular for phase shifters or LC based antenna elements in the micro wave (MW) region.

Mixture Example M-2

| | Composition | | | |
|---|---|---|---|---|
| | Compound | | | |
| No | Abbreviation | Conc./[mass-%] | Physical Properties | |
| 1 | PU-3-S | 20.0 | T(N, I) [° C.]= | 128 |
| 2 | PGU-3-S | 20.0 | $\varepsilon_{\parallel}$(20° C., 1 kHz)= | 28.6 |
| 3 | PGU-4-S | 20.0 | $\Delta\varepsilon$(20° C., 1 kHz)= | 23.6 |
| 4 | CPU-2-S | 20.0 | $\gamma_1$ (20° C.)/mPa · s= | 318 |
| 5 | CPU-3-S | 20.0 | $k_1$= | 13.7 |
| $\Sigma$ | | 100.0 | $k_3$= | 18.6 |
| | | | $V_0$ [V]= | 0.80 |
| | | | $\tan\delta_{\varepsilon r,\perp}$ (20° C., 19 GHz)= | 0.0133 |
| | | | $\tan\delta_{\varepsilon r,\parallel}$ (20° C., 19 GHz)= | 0.0070 |
| | | | $\tau$ (20° C., 19 GHz)= | 0.301 |
| | | | $\varepsilon_{r,\parallel}$ (20° C., 19 GHz)= | 3.4113 |
| | | | $\varepsilon_{r,\perp}$ (20° C., 19 GHz)= | 2.3842 |
| | | | $\eta$ (20° C., 19 GHz)= | 22.6 |

The mixture M-2 comprises 100% of compounds of formula I. This mixture is very well suitable for applications in the microwave range, in particular for phase shifters or LC based antenna elements in the micro wave (MW) region.

Mixture Example M-3

Composition

| No | Compound Abbreviation | Conc. [mass-%] | Physical Properties | |
|---|---|---|---|---|
| 1 | PU-3-S | 20.0 | T(N, I) [° C.]= | 133 |
| 2 | PGU-3-S | 12.0 | $\varepsilon_{\parallel}$(20° C., 1 kHz)= | 27.1 |
| 3 | PGU-4-S | 9.0 | $\Delta\varepsilon$(20° C., 1 kHz)= | 22.4 |
| 4 | PGU-5-S | 9.0 | $\gamma_1$ (20° C.)/ mPa·s= | 331 |
| 5 | CPU-2-S | 15.0 | $k_1$= | 14.5 |
| 6 | CPU-3-S | 10.0 | $k_3$= | 22.2 |
| 7 | CPU-4-S | 15.0 | $V_0$ [V]= | 0.85 |
| 8 | CPU-5-S | 10.0 | | |
| Σ | | 100.0 | tan $\delta_{\varepsilon r, \perp}$ (20° C, 19 GHz)= | 0.0135 |
| | | | tan $\delta_{\varepsilon r, \parallel}$ (20° C., 19 GHz)= | 0.0070 |
| | | | τ (20° C., 19 GHz)= | 0.267 |
| | | | $\varepsilon_{r, \parallel}$ (20° C., 19 GHz)= | 3.4771 |
| | | | $\varepsilon_{r, \perp}$ (20° C., 19 GHz)= | 2.5471 |
| | | | η (20° C., 19 GHz)= | 19.8 |

The mixture M-3 comprises 100% of compounds of formula I. This mixture is very well suitable for applications in the microwave range, in particular for phase shifters or LC based antenna elements in the micro wave (MW) region.

Mixture Example 4

Composition

| No | Compound Abbreviation | Conc./ [mass-%] | Physical Properties | |
|---|---|---|---|---|
| 1 | PU-3-S | 24.0 | T(N, I) [° C.]= | 125 |
| 2 | PGU-3-S | 10.0 | $\varepsilon_{\parallel}$(20° C., 1 kHz)= | 26.7 |
| 3 | PGU-4-S | 8.0 | $\Delta\varepsilon$(20° C., 1 kHz)= | 22.0 |
| 4 | PGU-5-S | 8.0 | $\gamma_1$ (20° C.)/ mPa·s= | 296 |
| 5 | CPU-2-S | 15.0 | $k_1$= | 13.8 |
| 6 | CPU-3-S | 10.0 | $k_3$= | 20.8 |
| 7 | CPU-4-S | 15.0 | $V_0$ [V]= | 0.83 |
| 8 | CPU-5-S | 10.0 | | |
| Σ | | 100.0 | tan $\delta_{\varepsilon r, \perp}$ (20° C., 19 GHz)= | 0.0134 |
| | | | tan $\delta_{\varepsilon r, \parallel}$ (20° C., 19 GHz)= | 0.0072 |
| | | | τ (20° C., 19 GHz)= | 0.286 |
| | | | $\varepsilon_{r, \parallel}$ (20° C., 19 GHz)= | 3.4169 |
| | | | $\varepsilon_{r, \perp}$ (20° C., 19 GHz)= | 2.4380 |
| | | | η (20° C., 19 GHz)= | 21.3 |

The mixture M-4 comprises 100% of compounds of formula I. This mixture is very well suitable for applications in the microwave range, in particular for phase shifters or LC based antenna elements in the micro wave (MW) region.

Mixture Example 5

Composition

| No | Compound Abbreviation | Conv./ [mass-%] | Physical Properties | |
|---|---|---|---|---|
| 1 | PU-3-S | 24.0 | T(N, I) [° C.]= | 123 |
| 2 | PGU-3-S | 12.0 | $\varepsilon_{\parallel}$(20° C., 1 kHz)= | 27.3 |
| 3 | PGU-4-S | 9.0 | $\Delta\varepsilon$(20° C., 1 kHz)= | 22.5 |
| 4 | PGU-5-S | 9.0 | $\gamma_1$ (20° C.)/ mPa·s= | 303 |
| 5 | CPU-2-S | 15.0 | $k_1$= | 13.8 |
| 6 | CPU-3-S | 9.0 | $k_3$= | 20.6 |
| 7 | CPU-4-S | 13.0 | $V_0$ [V]= | 0.83 |
| 8 | CPU-5-S | 9.0 | | |
| Σ | | 100.0 | tan $\delta_{\varepsilon r, \perp}$ (20° C., 19 GHz)= | 0.0135 |
| | | | tan $\delta_{\varepsilon r, \parallel}$ (20° C., 19 GHz)= | 0.0073 |
| | | | τ (20° C., 19 GHz)= | 0.288 |
| | | | $\varepsilon_{r, \parallel}$ (20° C., 19 GHz)= | 3.4259 |
| | | | $\varepsilon_{r, \perp}$ (20° C., 19 GHz)= | 2.4403 |
| | | | η (20° C., 19 GHz)= | 21.3 |

The mixture M-5 comprises 100% of compounds of formula I. This mixture is very well suitable for applications in the microwave range, in particular for phase shifters or LC based antenna elements in the micro wave (MW) region.

In the following tables the physical properties of the Comparative Examples C-1 and C-2 and the Examples M-1 to M-5 are summarised. All values are determined at 20° C. and 19 GHz.

| | Mixture | |
|---|---|---|
| | C-1 | C-2 |
| tan $\delta_{\varepsilon r, \perp}$ | 0.0189 | 0.0120 |
| tan $\delta_{\varepsilon r, \parallel}$ | 0.0091 | 0.0066 |
| τ | 0.336 | 0.318 |
| $\varepsilon_{r, \parallel}$ | N/A | 3.48 |
| $\varepsilon_{r, \perp}$ | N/A | 2.37 |
| Δε | 5.1 | 1.11 |
| η | 17.9 | 26.5 |

| | Mixture | | | | |
|---|---|---|---|---|---|
| | M-1 | M-2 | M-3 | M-4 | M-5 |
| tan $\delta_{\varepsilon r, \perp}$ | 0.0128 | 0.0133 | 0.0135 | 0.0134 | 0.0135 |
| tan $\delta_{\varepsilon r, \parallel}$ | 0.0069 | 0.0070 | 0.0070 | 0.0072 | 0.0073 |
| τ | 0.291 | 0.301 | 0.267 | 0.286 | 0.288 |
| $\varepsilon_{r, \parallel}$ | 3.3697 | 3.4113 | 3.4771 | 3.4169 | 3.4259 |
| $\varepsilon_{r, \perp}$ | 2.3886 | 2.3842 | 2.5471 | 2.4380 | 2.4403 |
| Δε | 0.9811 | 1.0271 | 0.9300 | 0.9789 | 0.9856 |
| η | 22.7 | 22.6 | 19.8 | 21.3 | 21.3 |

Surprisingly, mixtures according to the present invention, which do not comprise stilbene or tolane derivatives can be achieved having improved or comparably good properties as mixtures known from the state of the art that are based on compounds of formula I in combination with stilbene or tolane derivatives. It can be seen that the mixtures according to the invention even show an improved material quality (η)

compared to the mixture C-1 known from the state of the art because of a much lower dielectric loss.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

The entire disclosure[s] of all applications, patents and publications, cited herein and of corresponding application No. EP 16194405.3, filed Oct. 18, 2016 are incorporated by reference herein.

The invention claimed is:

1. A liquid-crystal medium, comprising
one or more compounds of formulae I-1 and I-2 and I-3,
wherein the total concentration of the one or more compounds of formulae I-1 and I-2 and I-3 in the medium is 73% to 100% by weight
and
wherein the concentration of the one or more compounds of formula I-2 in the medium is 25% to 40% by weight, and the concentration of the one or more compounds of formula I-3 in the medium is 45% or more by weight
or
wherein the concentration of the one or more compounds of formula I-3 in the medium is more than 50% by weight

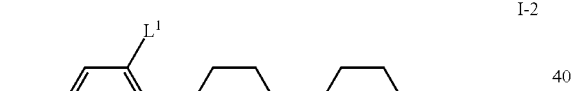

I-1

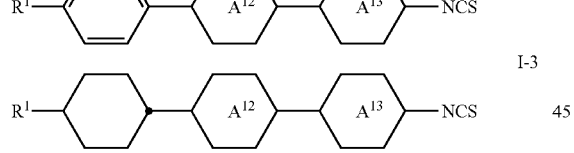

I-2

I-3 in which
R$^1$ denotes alkyl having 1 to 7 C atoms or alkenyl having 2 to 7 C atoms,
L$^1$ denotes H or F,

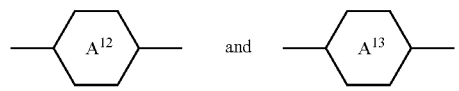 and independently of one another, denote

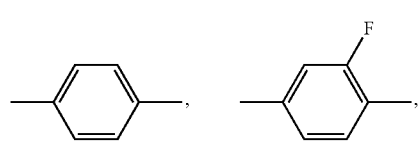

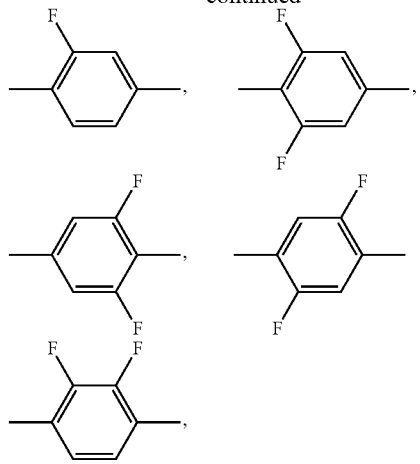

and
one or more compounds of formulae II and/or III,
wherein the concentration of the one or more compounds of formulae II and/or III is 0% to 27% by weight

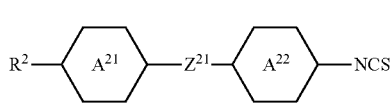

II

III

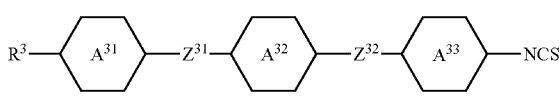

in which
R$^2$ denotes H, alkyl or alkoxy having 1 to 17 C atoms or alkenyl, alkenyloxy or alkoxyalkyl having 2 to 15 C atoms,
z$^{21}$ denotes trans-CH=CH—, trans-CF=CF— or —C≡C—

denotes

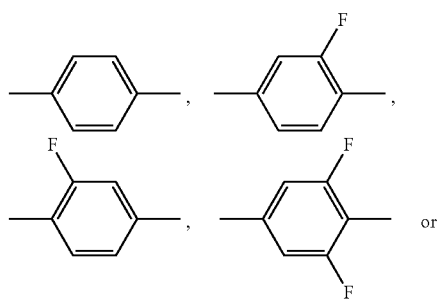

-continued

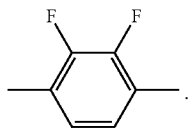

denotes

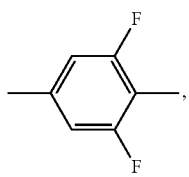

R³ denotes H, alkyl or alkoxy having 1 to 17 C atoms or alkenyl, alkenyloxy or alkoxyalkyl having 2 to 15 C atoms,
one of
Z³¹ and Z³² denotes trans-CH=CH-, trans-CF=CF— or
and the other
one of
Z³¹ and Z³² denotes trans-CH=CH—, trans-CF=CF— or a single bond,

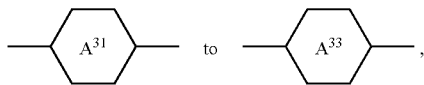

independently of one another, denote

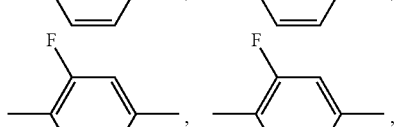

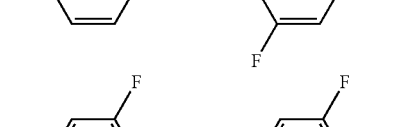

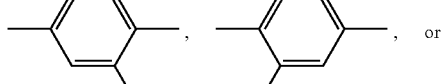

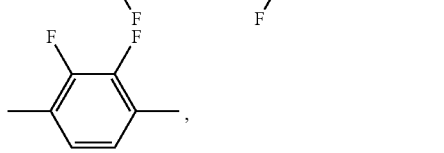, or

-continued

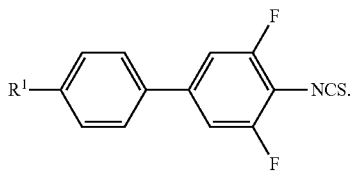

alternatively independently denotes

[three cyclohexyl ring structures] or .

2. A medium according to claim 1, which comprises one or more compounds of formulae I-3a to I-3d:

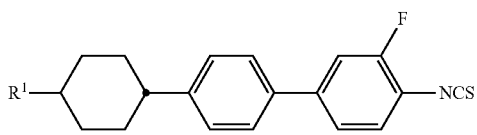

I-3a

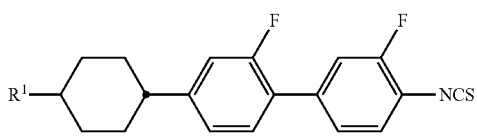

I-3b

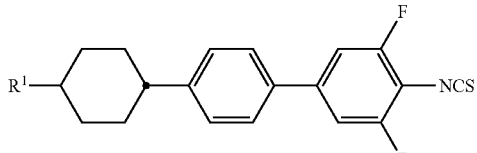

I-3c

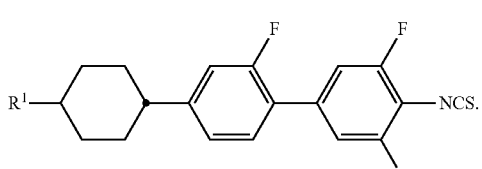

I-3d

3. A medium according to claim 2, which comprises one or more compounds of formula I-3c in a total concentration of 30% to 70% by weight.

4. A medium according to claim 1, which comprises a compound of formula I-1 in a total concentration of 20% or more.

5. A medium according to claim 1, wherein the one or more compounds of formula I-1 are of formula I-1b I-1b

[structure of I-1b showing R¹–cyclohexyl–phenyl–difluorophenyl–NCS]

6. A medium according to claim 1, which additionally comprises one or more chiral compounds.

7. A liquid-crystal medium, comprising one or more compounds of formula I

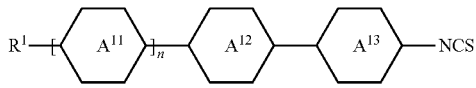

in which
R¹ denotes H, alkyl or alkoxy having 1 to 17 C atoms or alkenyl, alkenyloxy or alkoxyalkyl having 2 to 15 C atoms,
n=2,
one of

denotes

and the other denotes

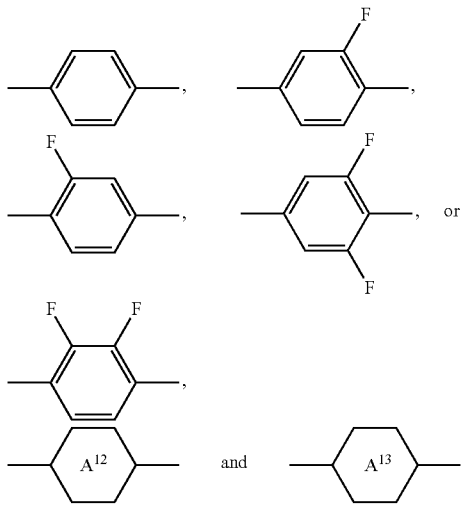

$A^{12}$ and $A^{13}$ independently of one another, denote

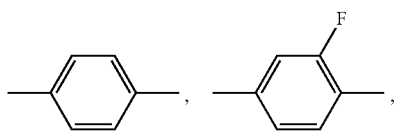

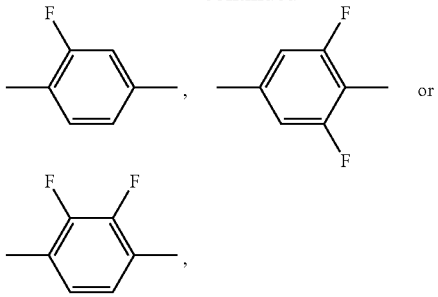

wherein the total concentration of the one or more compounds of formula I in the medium is 73% or more by weight.

8. A component for high-frequency technology, which comprises a liquid crystal medium according to claim 1.

9. A component according to claim 8, which is suitable for operation in the microwave range.

10. A component according to claim 8, which is a phase shifter or an LC based antenna element operable in the microwave region.

11. A process for the preparation of a liquid-crystal medium according to claim 1, comprising mixing together one or more compounds of formulae I-1 and I-2 and I-3, and optionally one or more compounds of formulae II and/or III, and optionally a chiral compound.

12. A microwave antenna array, which comprises one or more components according to claim 8.

13. A medium according to claim 1, where the total concentration of the one or more compounds of formulae I-1 and I-2 and I-3 in the medium is 80-90% by weight.

14. A medium according to claim 1, wherein the concentration of the one or more compounds of formula I-2 in the medium is 25% to 40% by weight, and the concentration of the one or more compounds of formula I-3 in the medium is 45% or more by weight.

15. A medium according to claim 1, wherein the concentration of the one or more compounds of formula I-3 in the medium is more than 50% by weight.

16. A medium according to claim 7, where the total concentration of the one or more compounds of formula I in the medium is 80-90% by weight.

17. A component for high-frequency technology, which comprises a liquid crystal medium according to claim 7.

18. A medium according to claim 1, which comprises one or more compounds of formulae II and/or III, wherein the concentration of the one or more compounds of formulae II and/or III is 2% to 20% by weight.

19. A liquid-crystal medium according to claim 1,
wherein the total concentration of the one or more compounds of formulae I-1 and I-2 and I-3 in the medium is 80% to 100% by weight
and
wherein the concentration of the one or more compounds of formulae II and/or III is 0% to 20% by weight.

20. A component for high-frequency technology, which comprises a liquid crystal medium according to claim 19.

* * * * *